United States Patent
Lanci et al.

(10) Patent No.: US 10,138,176 B2
(45) Date of Patent: Nov. 27, 2018

(54) PRODUCTION AND SEPARATION OF 3,3'-, 3,4'- AND 4,4'-DIMETHYL BIPHENYL ISOMERS

(71) Applicant: ExxonMobil Research and Engineering Company, Annandale, NJ (US)

(72) Inventors: Michael P. Lanci, Flemington, NJ (US); Changyub Paek, Bridgewater, NJ (US); Catherine M. Dorsi, Houston, TX (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 0 days.

(21) Appl. No.: 15/886,408

(22) Filed: Feb. 1, 2018

(65) Prior Publication Data

US 2018/0222817 A1    Aug. 9, 2018

Related U.S. Application Data

(60) Provisional application No. 62/453,190, filed on Feb. 1, 2017.

(51) Int. Cl.
   *C07C 2/74* (2006.01)
   *C07C 5/42* (2006.01)
   (Continued)

(52) U.S. Cl.
   CPC .......... *C07C 2/74* (2013.01); *C07C 2/66* (2013.01); *C07C 5/10* (2013.01); *C07C 5/2732* (2013.01); *C07C 5/367* (2013.01)

(58) Field of Classification Search
   CPC .... C07C 2/74; C07C 5/42; C07C 7/12; C07C 7/13
   (Continued)

(56) References Cited

U.S. PATENT DOCUMENTS

| | | | |
|---|---|---|---|
| 3,626,020 A | 12/1971 | Neuzil | |
| 3,699,182 A | 10/1972 | Cattanach | |

(Continued)

FOREIGN PATENT DOCUMENTS

| | | |
|---|---|---|
| WO | 2014117076 A1 | 7/2014 |
| WO | 2014117076 A9 | 7/2015 |

(Continued)

OTHER PUBLICATIONS

Baertsch et al., "Permeation of aromatic hydrocarbon vapors through silicalite-zeolite membranes", J. Phys. Chem, 1996, vol. 100, pp. 7676-7679.

(Continued)

*Primary Examiner* — Thuan D Dang
(74) *Attorney, Agent, or Firm* — Kristina Okafor

(57) ABSTRACT

In a process for producing one or more 3,3'-, 3,4'- and 4,4'-dimethyl biphenyl isomers, a feed comprising toluene is contacted with hydrogen in the presence of a hydroalkylation catalyst under conditions effective to produce a hydroalkylation reaction product comprising (methylcyclohexyl)toluenes. At least part of the hydroalkylation reaction product is dehydrogenated in the presence of a dehydrogenation catalyst under conditions effective to produce a dehydrogenation reaction product comprising a mixture of dimethyl biphenyl isomers. The dehydrogenation reaction product is then separated into at least a first stream containing one or more 3,3'-, 3,4'- and 4,4'-dimethyl biphenyl isomers and at least one second stream comprising one or more 2,X'-dimethyl biphenyl isomers (where X is 2, 3, or 4). The 3,3'-, 3,4'- and 4,4'-dimethyl biphenyl isomers are then separated utilizing selective adsorption.

17 Claims, 16 Drawing Sheets

(51) Int. Cl.
　　　*C07C 7/12*　　　(2006.01)
　　　*C07C 7/13*　　　(2006.01)
　　　*C07C 5/367*　　 (2006.01)
　　　*C07C 5/27*　　　(2006.01)
　　　*C07C 5/10*　　　(2006.01)
　　　*C07C 2/66*　　　(2006.01)

(58) Field of Classification Search
　　　USPC .............. 585/323, 454, 440, 826, 827, 828
　　　See application file for complete search history.

(56) References Cited

U.S. PATENT DOCUMENTS

| | | | |
|---|---|---|---|
| 5,202,516 A * | 4/1993 | Lee | ................... B01J 29/18 585/467 |
| 6,730,625 B1 | 5/2004 | Chang et al. | |
| 8,580,120 B2 | 11/2013 | Porter | |
| 9,085,669 B2 | 7/2015 | Dakka et al. | |
| 9,328,053 B2 | 5/2016 | Bai et al. | |
| 9,580,572 B2 | 2/2017 | Dakka et al. | |
| 9,663,417 B2 | 5/2017 | Dakka et al. | |
| 9,688,602 B2 | 6/2017 | Dakka et al. | |
| 9,896,393 B2 | 2/2018 | Salciccioli et al. | |
| 2009/0326310 A1 | 12/2009 | Kulprathipanja et al. | |
| 2014/0275609 A1 * | 9/2014 | Dakka | ...................... C07C 5/367 560/102 |
| 2016/0176785 A1 | 6/2016 | Salciccioli et al. | |

FOREIGN PATENT DOCUMENTS

WO　　　2015112252 A1　　7/2015
WO　　　20150191289 A1　12/2015

OTHER PUBLICATIONS

Foster et al., "A geometric solution to the largest-free-sphere problem in zeolite frameworks", Micropo. Mesopor. Mat., 2006, vol. 90, pp. 32-38.

Funke et al., "Separation of close-boiling hydrocarbons with silicalite zeolite", J. Chem. Soc. Faraday Trans., 1996, vol. 92, pp. 2499-2502.

Minceva et al., "Modeling and simulation of a simulated moving bed for the separation of p-xylene", Ind. Eng. Chem. Res., 2002, vol. 41, pp. 3454-3461.

Minceva et al., "Understanding and revamping of industrial scale SMB units for p-xylene separation", AIChE Journal, 2007, vol. 53, pp. 138-149.

Pais et al., "Chiral separation by SMB chromatography", Sep. Pur. Tech., 2000, vol. 20, pp. 67-77.

Rajendran et al., "Simulated moving bed chromatography for the separation of enantiomers", J. Chrom. A, 2009, vol. 1216, pp. 709-738.

Silva et al., "Fixed-bed adsorption of aromatic C8 isomers: Breakthrough experiments, modeling and simulation", 2012, vol. 90, pp. 246-256.

Silva et al., "Modeling and simulation of an industrial-scale parex process", AIChE Journal, 2015, vol. 61, pp. 1345-1363.

Tokay et al., "Nanopaiticle silicalite-1 crystallization from clear solutions: Nucleation", Micropor. Mesopor. Mat., 2009, vol. 118, pp. 143-151.

Ruthven et al., "Counter-Current and Simulated Counter-Current Adsorption Separation Processes", Chem. Eng. Sci., 1989, vol. 44, pp. 1011-1038.

* cited by examiner

PRODUCTION AND SEPARATION OF 3,3'-, 3,4'- AND 4,4'-DIMETHYL BIPHENYL ISOMERS

CROSS-REFERENCE TO RELATED APPLICATIONS

This application claims the benefit of U.S. Provisional Application No. 62/453,190, filed on Feb. 1, 2017, the entire contents of which are incorporated herein by reference.

FIELD

This disclosure relates to the production and separation of 3,3'-, 3,4'- and 4,4'-dimethyl biphenyl isomers, wherein separation is facilitated by selective adsorption.

BACKGROUND

Dimethyl biphenyl (DMBP) compounds are useful intermediates in the production of a variety of commercially valuable products, including polyesters and plasticizers for PVC and other polymer compositions. DMBP compounds can be readily converted to an ester plasticizer by a process comprising oxidation of the DMBP to produce the corresponding mono- or dicarboxylic acid followed by esterification with a long chain alcohol.

For example, 4,4'-biphenyl-dicarboxylic acid, optionally together with 3,4'-biphenyl dicarboxylic acid, is a potential precursor, either alone or as a modifier for polyethylene terephthalate (PET), in the production of polyester fibers, engineering plastics, liquid crystal polymers for electronic and mechanical devices, and films with high heat resistance and strength.

Processes to produce DMBP compounds generally yield a mixture of all six DMBP isomers, namely 2,2'-, 2,3'-, 2,4'-, 3,3'-, 3,4'- and 4,4'-DMBP (see, for example, International Patent Application Publication No. WO 2015/112252).

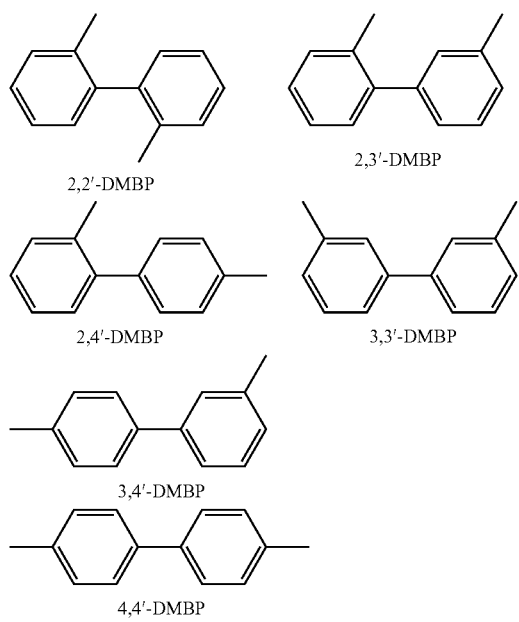

However, for certain applications, it is desirable to maximize the purity of individual isomers, particularly the 3,3'-, 3,4'- and 4,4'-isomers.

Based on boiling point differences it is possible to separate the 3,3'-, 3,4'- and 4,4'-isomers from the 2,X' isomers, where X=2, 3 or 4, utilizing, for example, fractional distillation. However, separation of the 3,3'-, 3,4'- and 4,4'-isomers from each other based on boiling point is more challenging, particularly separation of the 3,4'-isomer from the 4,4'-isomer which have very close boiling points (see Table 1 below).

TABLE 1

| Isomer | Normal Boiling Point (° C.) | Fusion Temperature (° C.) |
| --- | --- | --- |
| 2,2' | 261 | 19 |
| 2,3' | 272 | |
| 2,4' | 275 | −24 |
| 3,3' | 289 | 8 |
| 3,4' | 293 | 12 |
| 4,4' | 296 | 115 |

Further, based on heat of fusion differences it is in principle possible in to effect separation of 3,3'-, 3,4'- and 4,4'-isomers via crystallization. However, because the relative proportions of some of these isomers in a given mixture may be small separation via crystallization may not be commercially attractive.

It is known that certain adsorbents, for example zeolites, can be used to separate individual hydrocarbons from mixtures thereof. Adsorptive separation may be useful where the components to be separated have similar physical properties such as boiling point and melting points. For example, utilizing zeolites it is possible to selectively separate a predetermined xylene from a mixture of xylene isomers. See, for example, United States Patent Application Publication No. 2009/0326310 and references therein.

In view of the above it would be desirable to provide alternative processes for the production and separation of DMBP isomers, particularly processes that may be amenable to commercial implementation.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

SUMMARY

In a first aspect of the present disclosure there is provided a process for producing one or more 3,3'-, 3,4'- and 4,4'-dimethyl biphenyl isomers, the process comprising:
(a) contacting a feed comprising toluene with hydrogen in the presence of a hydroalkylation catalyst under conditions effective to produce a hydroalkylation reaction product comprising (methylcyclohexyl)toluenes;
(b) dehydrogenating at least part of the hydroalkylation reaction product in the presence of a dehydrogenation catalyst under conditions effective to produce a dehydrogenation reaction product comprising said dimethyl biphenyl isomers;
(c) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and (d) separating the 3,3'-, 3,4'- and 4,4'-dimethyl biphenyl isomers, wherein said separation comprises at least one selective adsorption.

In a second aspect of the present disclosure there is provided a process for producing one or more 3,3'-, 3,4'- and 4,4'-dimethyl biphenyl isomers, the process comprising:
(a) contacting a feed comprising benzene with hydrogen in the presence of a hydroalkylation catalyst under conditions effective to produce a hydroalkylation reaction product comprising cyclohexylbenzenes;
(b) dehydrogenating at least part of the hydroalkylation reaction product in the presence of a dehydrogenation catalyst under conditions effective to produce a dehydrogenation reaction product comprising biphenyl;
(c) reacting at least part of the dehydrogenation reaction product with a methylating agent in the presence of an alkylation catalyst under conditions effective to produce a methylation reaction product comprising said dimethyl biphenyl isomers;
(d) separating the methylation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and
(e) separating the 3,3'-, 3,4'- and 4,4'-dimethyl biphenyl isomers, wherein said separation comprises at least one selective adsorption.

In a third aspect of the present disclosure there is provided a process for producing one or more 3,3'-, 3,4'- and 4,4'-dimethyl biphenyl isomers, the process comprising:
(a) oxidizing a feed comprising benzene in the presence of an oxidative coupling catalyst under conditions effective to produce an oxidation reaction product comprising biphenyl;
(b) reacting at least part of the oxidation reaction product with methylating agent in the presence of an alkylation catalyst under conditions effective to produce a methylation reaction product comprising said dimethyl biphenyl isomers;
(c) separating the methylation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and
(d) separating the 3,3'-, 3,4'- and 4,4'-dimethyl biphenyl isomers, wherein said separation comprises at least one selective adsorption.

In a fourth aspect of the present disclosure there is provided a process for producing one or more 3,3'-, 3,4'- and 4,4'-dimethyl biphenyl isomers, the process comprising:
(a) thermally treating a feed comprising benzene under conditions effective to produce a dehydrocondensation product comprising biphenyl;
(b) reacting at least part of the dehydrocondensation product with methylating agent in the presence of an alkylation catalyst under conditions effective to produce a methylation reaction product comprising said dimethyl biphenyl isomers;
(c) separating the methylation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and
(d) separating the 3,3'-, 3,4'- and 4,4'-dimethyl biphenyl isomers, wherein said separation comprises at least one selective adsorption.

In any of the first to fourth aspects the separation into at least a first stream and at least one second stream may comprise distillation and/or crystallization.

In any of the first to fourth aspects the separation of the 3,3'-, 3,4'- and 4,4'-dimethyl biphenyl isomers in the first stream may comprise:
(i) contacting the first stream with a first adsorbent thereby selectively adsorbing at least one of the 3,3'-, 3,4'- and 4,4'-dimethyl biphenyl isomers within the adsorbent;
(ii) withdrawing from said first adsorbent a raffinate stream comprising less selectively adsorbed dimethyl biphenyl isomers; and
(iii) withdrawing from said first adsorbent a first extract stream comprising said selectively adsorbed dimethyl biphenyl isomers.

The separation of the 3,3'-, 3,4'- and 4,4'-dimethyl biphenyl isomers may further comprise:
(i) contacting the raffinate stream with a second adsorbent thereby selectively adsorbing one of the dimethyl biphenyl isomers less selectively adsorbed by the first adsorbent; and
(ii) withdrawing from said second adsorbent a second extract stream comprising a less selectively adsorbed dimethyl biphenyl isomer and a third extract stream comprising said selectively adsorbed dimethyl biphenyl isomer.

Alternatively, the separation of the 3,3'-, 3,4'- and 4,4'-dimethyl biphenyl isomers may further comprise selectively crystallizing one of the dimethyl biphenyl isomers from the raffinate stream.

In any of the first to fourth aspects the separation of the 3,3'-, 3,4'- and 4,4'-dimethyl biphenyl isomers in the first stream may comprise:
(i) separating by crystallization at least one of the isomers to provide a solid product and a raffinate stream comprising non-crystallizing isomers;
(ii) contacting the raffinate stream with an adsorbent thereby selectively adsorbing at least one of the non-crystallizing isomers within the adsorbent;
(iii) withdrawing from said adsorbent an extract stream comprising the less selectively adsorbed dimethyl biphenyl isomer or isomers; and
(iv) withdrawing from said adsorbent another extract stream comprising said selectively adsorbed dimethyl biphenyl isomer or isomers.

In any of the herein disclosed aspects the process may further comprise contacting the second stream comprising one or more 2,X'-dimethyl biphenyl isomers (where X=2, 3 or 4) with a hydrogenation catalyst under conditions effective to produce one or more methylcyclohexyl toluene isomers, contacting the said methylcyclohexyl toluene isomers with a transalkylation catalyst under conditions effective to modify the methylcyclohexyl toluene isomer distribution and contacting the said modified methylcyclohexyl toluene isomer distribution with a dehydrogenation catalyst to provide one or more 3,3'-, 3,4'- and/or 4,4' dimethyl biphenyl isomers. The hydrogenation and transalkylation may be performed in a single reactor or in separate reactors.

In any of the herein disclosed aspects the process may further comprise contacting any one or more of the herein disclosed raffinate streams comprising 3,3'-, 3,4'- or 4,4'-dimethyl biphenyl isomers with a hydrogenation catalyst under conditions effective to produce one or more methylcyclohexyl toluene isomers, contacting the said methylcyclohexyl toluene isomers with a transalkylation catalyst under conditions effective to modify the methylcyclohexyl toluene isomer distribution and contacting the said modified methylcyclohexyl toluene isomer distribution with a dehydrogenation catalyst to provide one or more 3,3'-, 3,4'- and/or 4,4'-dimethyl biphenyl isomers. The hydrogenation and transalkylation may be performed in a single reactor or in separate reactors.

In any of the herein disclosed aspects the process may further comprise contacting one or more extract streams from the first and/or second adsorbent with a hydrogenation catalyst under conditions effective to produce one or more methylcyclohexyl toluene isomers, contacting the said methylcyclohexyl toluene isomers with a transalkylation catalyst under conditions effective to modify the methylcyclohexyl toluene isomer distribution and contacting the said modified methylcyclohexyl toluene isomer distribution with a dehydrogenation catalyst so as to provide one or more 3,3'-, 3,4'- and/or 4,4'-dimethyl biphenyl isomers. The hydrogenation and transalkylation may be performed in a single reactor or in separate reactors.

In some embodiments the hydrogenation catalyst and the transalkylation catalyst are the same catalyst. In other embodiments the hydrogenation catalyst and the transalkylation catalyst are different catalysts.

In the herein disclosed first aspect the process may further comprise feeding at least part of the modified methylcyclohexyl toluene isomer distribution from one or more of the transalkylation steps discussed above to the dehydrogenation step (b).

In any one of the herein disclosed aspects the process may further comprise contacting at least part of any one or more of the raffinate streams with an isomerization catalyst under conditions effective to produce a mixture of isomers comprising the previously extracted dimethyl biphenyl isomer(s).

In any one of the herein disclosed aspects the process may further comprise contacting at least part of any one or more of the extract streams with an isomerization catalyst under conditions effective to produce a mixture of isomers comprising the previously extracted dimethyl biphenyl isomer(s).

At least part of the so produced mixture of 3,3'-, 3,4'- and 4,4'-dimethyl biphenyl isomers may be fed to the separation step of any one of the herein disclosed aspects which affords at least a first stream and at least one second stream.

At least part of the so produced mixture of 3,3'-, 3,4'- and 4,4'-dimethyl biphenyl isomers may be fed to the first adsorption unit or alternatively may be subjected to crystallization to separate at least one of the isomers.

Suitable isomerization catalysts include, but are not limited to, zeolites having a largest diffuse along diameter of 4.5 to 8 Å or greater than 4.8 Å.

In any of the herein disclosed aspects or embodiments the step of contacting with an adsorbent may occur in the presence of one or more solvents.

The solvent may comprise an aromatic hydrocarbon, a saturated hydrocarbon or combinations thereof.

In any of the herein disclosed aspects the first stream comprising the 2,X'-DMBP isomers, where X=2, 3 or 4, may further comprise one or more of cyclopentadienyl toluenes (CPDTs), 4-methylcyclohexyl toluenes (4,X'-MCHTs), 3-methylcyclohexyl toluenes (3,X'-MCHTs), 2-methylcyclohexyl toluenes (2,X'-MCHT), ethyl or dimethyl cyclopentyl toluenes (CPTs), 1-methylcyclohexyl toluenes (1,X'-MCHTs) and dimethyl bicyclohexanes (DMBCHs).

In any of the herein disclosed aspects the feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) may comprise 5-50% by weight 3,3'-isomer, 5-80% by weight 3,4'-isomer and 5-90% by weight 4,4'-isomer based on the total weight of the three isomers.

In any of the herein disclosed aspects the feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) may comprise 10-40% by weight 3,3'-isomer, 20-70% by weight 3,4'-isomer and 5-30% by weight 4,4'-isomer based on the total weight of the three isomers.

In any of the herein disclosed aspects the feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) may comprise 15-35% by weight 3,3'-isomer, 40-70% by weight 3,4'-isomer and 5-30% by weight 4,4'-isomer based on the total weight of the three isomers.

In any of the herein disclosed aspects the isomerization catalyst contact product may comprise 10-60% by weight 3,3'-isomer, 10-60% by weight 3,4'-isomer, 2-30% by weight 4,4'-isomer and 2-30% by weight 2,X'-isomers (where X=2, 3 or 4) based on the total weight of the isomers.

The isomerization catalyst contact product may comprise 20-55% by weight 3,3'-isomer, 20-55% by weight 3,4'-isomer, 5-20% by weight 4,4'-isomer and 5-25% by weight 2,X'-isomers (where X=2, 3 or 4) based on the total weight of the isomers.

The isomerization catalyst contact product may comprise about 37% by weight 3,3'-isomer, about 38% by weight 3,4'-isomer, about 10% by weight 4,4'-isomer and about 13% by weight 2,X'-isomers (where X=2, 3 or 4) based on the total weight of the isomers.

The at least one adsorptive separation may comprise a simulated moving bed, membrane separation or semi-batch (swing) adsorption.

In another aspect of the present disclosure there is provided a process for separating one or more dimethyl biphenyl isomers 3,3'-, 3,4'- and 4,4'-DMBP from a feed comprising two or more of said isomers, wherein the separation comprises one or more selective adsorptions.

In some embodiments the feed is derived from separation of a stream comprising one or more dimethyl biphenyl isomers 3,3'-, 3,4'- and 4,4'-DMBP, and one or more 2,X'-dimethyl biphenyl isomers (where X=2, 3 or 4).

In any of the herein disclosed processes the isolated 3,3'-, 3,4'- and 4,4'-dimethyl biphenyl isomers may be subjected to oxidation to produce a dicarboxylic acid product.

The dicarboxylic acid may be reacted with a diol to produce a polyester product.

The carboxylic acid acid may be reacted with an alcohol to produce an esterification product.

Advantageously, as the 3,3'-, 3,4'- and 4,4'-dimethyl biphenyl isomers may be produced in high purity by the processes of the present disclosure, access to isomerically pure dicarboxylic acids and subsequent esterification products is possible.

In some embodiments of the present disclosure the first adsorbent may comprise more than one adsorbent type, each having a different adsorptive capacity for a particular dimethyl biphenyl isomer.

In some embodiments of the present disclosure the first and second adsorbents may be in a single vessel or, alternatively, in separate vessels.

In some embodiments of the present disclosure the first and second adsorbents may be arranged in series.

In other embodiments the first and second adsorbents may be arranged in parallel. In series or parallel operation, different adsorbents may be utilized as first and second adsorbents.

In some embodiments the adsorbent of the present disclosure is a zeolite or zeolite analogue.

As used herein the term 'zeolite', as well as encompassing aluminosilicate materials, also encompasses zeolite analogues where one or more of the framework aluminum or silicon atoms are replaced by another atom, such as, for example, boron, gallium, germanium, magnesium, titanium, phosphorus, nitrogen or sulfur.

Some embodiments of the present disclosure relate to the discovery that adsorbents comprising zeolites, wherein said zeolites comprise one or more metal cations in the +1 or +2 oxidation states, are capable of selectively adsorbing one or more of 3,3'-, 3,4'- and 4,4'-dimethyl biphenyl isomers from mixtures thereof.

Other embodiments of the present disclosure relate to the discovery that adsorbents comprising zeolites, wherein said zeolites have a largest diffuse along dimension of at least about 4 Angstroms (Å), and wherein said zeolites are substantially free of metal cations in the +1 or +2 oxidation states, are capable of selectively adsorbing the 4,4'-dimethyl biphenyl isomer from mixtures of two or more of 3,3'-, 3,4'- and 4,4'-dimethyl biphenyl isomers.

As used herein the term 'largest diffuse along dimension' refers to a measure of the largest dimension of a zeolite channel system based on the diameter of the largest possible free-sphere that can diffuse along dimensions a, b or c of a zeolite channel and which are computed geometrically by Delaunay triangulation as detailed in: "A geometric solution to the largest-free-sphere problem in zeolite frameworks", M. D. Foster, I. Rivin, M. M. J. Treacy and O. Delgado Friedrichs, *Micropor. Mesopor. Mat.*, 90, 32-38, 2006.

Yet further embodiments of the present disclosure relate to the discovery that particular solvents, when utilized in the adsorptive separations, enhance the selectivity for the adsorption of one or more of 3,3'-, 3,4'- and 4,4'-dimethyl biphenyl isomers.

Metal Cation Containing Zeolites

In some embodiments the adsorbent is at least one zeolite, wherein said zeolite comprises one or more metal cations in the +1 or +2 oxidation states.

Said zeolite may have a largest diffuse along dimension of at least about 4 Angstroms (Å).

The largest diffuse along dimension of the zeolite may be at least about 4.5 Å, or at least about 5.0 Å, or at least about 5.5 Å, or at least about 6.0 Å, or at least about 6.5 Å, or at least about 7.0 Å.

The largest diffuse along dimension of the zeolite may be between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

The zeolite structure type may comprise BEA, FAU, MFI, MEL, MTW, MOR, LTL, EMT, FER, MAZ, MEI, TON, MWW, EUO, MFS, IMF, MRE, ITN, MSE, MTT or IWV.

The zeolite may comprise a 12-ring zeolite, an 11-ring zeolite or a 10-ring zeolite.

The zeolite may comprise an X or Y type zeolite or a Beta type zeolite.

In some embodiments the Si/Al ratio of the zeolite may be less than about 200, or less than about 100, or less than about 50, or less than about 20, or less than about 10. The Si/Al ratio may preferably be less than about 10.

In some embodiments the Si/Al ratio of the zeolite may be between about 1 and about 4, or between about 1.5 and about 3.5, or between about 2 and about 3.

The zeolite may comprise one or more alkali metal cations, alkaline earth metal cations, transition metal cations, rare earth metal cations or combinations thereof.

The zeolite may comprise one or more alkali metal cations, alkaline earth metal cations or combinations thereof.

The zeolite may comprise one or more of $Na^+$, $K^+$, $Rb^+$, $Cs^+$, $Mg^{2+}$, $Ca^{2+}$, $Sr^{2+}$ and $Ba^{2+}$ cations.

The zeolite may comprise one or more metal cations, wherein the ionic radius of the metal cation is between about 0.8 Å and about 2.0 Å.

In some embodiments the molar ratio of all metal cations in the +1 and/or +2 oxidation states relative to aluminum in the zeolite may be between about 0.01 and about 2.0, or between about 0.05 and about 1.5, or between about 0.1 and about 1.5, or between about 0.25 and about 1.5.

In some embodiments the molar ratio of all metal cations in the +1 and/or +2 oxidation states relative to aluminum in the zeolite may be greater than about 0.27, or greater than about 0.30, or greater than about 0.40, or greater than about 0.45, or greater than about 0.50.

In some embodiments the zeolites used to prepare the adsorbents of the present disclosure contain residual amounts of sodium cations. This is because the originally prepared zeolite may have used sodium containing compounds in its synthesis, for example in the case of a Y type zeolite. The amount of residual sodium cations may depend on the level of other metal cation exchange that has occurred during the cation exchange process.

In some embodiments the Na/Al molar ratio of the zeolite is less than about 1.0, or less than about 0.8, or less than about 0.6, or less than about 0.4, or less than about 0.3 when the zeolite contains at least one other metal cation.

In some embodiments the molar ratio of metal cations in the +1 and/or +2 oxidation states other than sodium, and relative to aluminum in the zeolite, may be greater than about 0.1, or greater than about 0.2, or greater than about 0.3, or greater than about 0.4. Preferably, the ratio is greater than about 0.3.

It has been discovered that metal cations modify the relative adsorption of the dimethyl biphenyl isomers to a degree that the order of preference for adsorption is changed.

It has also been discovered that the crystallite size of the zeolite may improve the adsorptive ability. Accordingly, smaller crystallite size may improve adsorptive ability of the zeolite for DMBP isomers.

The average crystallite size of the zeolite may be less than about 5000 nm, or less than about 2000 nm, or less than about 1000 nm, or less than about 500 nm, or less than about 200 nm, or less than about 100 nm, or less than about 50 nm.

The average crystallite size of the zeolite may be from about 1 to about 5000 nm, or from about 1 to about 1000 nm, or from about 5 to about 500 nm, or from about 10 to about 100 nm.

In some embodiments the processes disclosed herein comprise an adsorptive separation which separates 3,3'-DMBP from a mixture comprising two or more of 3,3'-DMBP, 3,4'-DMBP and 4,4'-DMBP.

In some embodiments the processes disclosed herein comprise an adsorptive separation which separates 3,4'-DMBP from a mixture comprising two or more of 3,3'-DMBP, 3,4'-DMBP and 4,4'-DMBP.

In some embodiments the processes disclosed herein comprise an adsorptive separation which separates 4,4'-DMBP from a mixture comprising two or more of 3,3'-DMBP, 3,4'-DMBP and 4,4'-DMBP.

In one embodiment the processes comprise an adsorptive separation which separates 3,3'-DMBP from a mixture comprising two or more of 3,3'-DMBP, 3,4'-DMBP and 4,4'-DMBP, wherein the adsorbent comprises at least one zeolite, said zeolite comprising one or more metal cations in the +1 or +2 oxidation states.

In one embodiment the processes comprise an adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising one or more metal cations in the +1 or +2 oxidation states.

In one embodiment the processes comprise an adsorptive separation which separates 4,4'-DMBP from a mixture comprising two or more of 3,3'-DMBP, 3,4'-DMBP and 4,4'-DMBP, wherein the adsorbent comprises at least one zeolite, said zeolite comprising one or more metal cations in the +1 or +2 oxidation states.

In other embodiments two different adsorbents which have different adsorption characteristics for the three DMBP isomers may be utilized. For example, in series operation.

A first selective adsorption may preferentially adsorb one of the 3,3'-, 3,4'- or 4,4'-dimethyl biphenyl isomers and a second selective adsorption may preferentially adsorb one of the 3,3'-, 3,4'- or 4,4'-dimethyl biphenyl isomers not preferentially adsorbed in the first selective adsorption.

The first selective adsorption may preferentially adsorb two of the 3,3'-, 3,4'- or 4,4'-dimethyl biphenyl isomers and after desorption of these isomers a second selective adsorption may preferentially adsorb one of them.

Accordingly, the use of two different adsorbents provides a process for separating a mixture of the three DMBP isomers into pure components.

Substantially Metal Cation Free Zeolites

The adsorbent may comprise at least one zeolite, wherein said zeolite has a largest diffuse along dimension of at least about 4 Angstroms (Å).

The zeolite may be substantially free of alkali metal cations and alkaline earth metal cations. The alkali metal cation and alkaline earth metal cation content may, in combination, be less than about 0.1 wt. %, or less than about 0.075 wt. %, or less than about 0.05 wt. %.

The largest diffuse along dimension of the zeolite may be at least about 4.5 Å, or at least about 5.0 Å, or at least about 5.5 Å, or at least about 6.0 Å, or at least about 6.5 Å, or at least about 7.0 Å.

The largest diffuse along dimension of the zeolite may be between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

Embodiments are directed to processes for separating 4,4'-DMBP from a mixture comprising 3,3'-DMBP, 3,4'-DMBP and 4,4'-DMBP. The mixture may be contacted under adsorption conditions with an adsorbent comprising, for example, ZSM-5 zeolite. Aspects of the disclosure are associated with the discovery that 'nano zeolites', for example, 'nano ZSM-5' (i.e., nano-size zeolite ZSM-5 crystallites having an average crystallite size below 1000 nm) provides highly advantageous performance characteristics when incorporated into adsorbents used in the adsorptive separation of 4,4'-DMBP. In particular, the mass transfer rate of 4,4'-DMBP into the zeolite pores is significantly greater, relative to zeolites synthesized according to conventional methods which typically have an average crystallite size on the order of 1-5 microns.

This increase in mass transfer rate in turn reduces the amount of adsorbent required to obtain a given flow rate of product (e.g., an extract product stream) from a given feed stream, for any desired set of performance parameters (e.g., 4,4'-DMBP purity and recovery). Process economics are therefore improved.

Adsorbents comprising the 'nano-zeolites, for example 'nano ZSM-5', may also have greater 4,4'-DMBP capacity with comparable selectivity, relative to adsorbents with larger average zeolite crystallite sizes.

The zeolite structure type may comprise BEA, FAU, MFI, MEL, MTW, MOR, LTL, EMT, FER, MAZ, MEI, TON, MWW, EUO, MFS, IMF, MRE, ITN, MTT, MSE or IWV.

The zeolite may comprise a 12-ring zeolite, an 11-ring zeolite or a 10-ring zeolite.

The zeolite may comprise a ZSM-5, or a ZSM-11, or a ZSM-57, or a ZSM-48 or a ZSM-12 type zeolite.

The zeolite may be a dealuminated zeolite or an aluminum free zeolite such as silicalite.

The Si/Al ratio of the zeolite may be greater than about 10, or greater than about 20, or greater than about 50, or greater than about 100, or greater than about 150, or greater than about 200.

The Si/Al ratio of the zeolite may be between about 10 and about 300 or between about 15 and about 250.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises one or more zeolites, said zeolite having an average crystallite size between 1 and 100 nm, and said zeolite being substantially free of metal cations in the +1 or +2 oxidation states.

Solvent Effects

Aspects of the present disclosure are based on the surprising discovery that solvent choice has an impact on the separation of the 3,3'-DMBP, 3,4'-DMBP and 4,4'-DMBP isomers.

In some embodiments of the processes of the present disclosure the degree of separation of the 3,3'-DMBP, 3,4'-DMBP and 4,4'-DMBP isomers may be based on the kinetic diameter of the solvent. The kinetic diameter may be derived from a spherical model or a smallest ellipsoid model. In other embodiments the degree of separation may be based on the polarity of the solvent. In yet other embodiments the degree of separation may be based on both the kinetic diameter of the solvent and its polarity. Accordingly, solvents which are bulkier (generally a larger kinetic diameter) may afford improved separation of the isomers, however this effect may be modulated by solvent polarity. Generally, single ring aromatic solvents such as benzene adsorb to the zeolite more strongly that saturated solvents.

Without wishing to be bound by theory it is believed that there is a tertiary interaction involving the DMBP isomers, the solvent and the zeolite pores which impact on the efficacy of selective adsorption of one or more of the DMBP isomers. Preferred solvents are those which do not significantly compete with a particular DMBP isomer in respect of adsorption into the pores of the zeolite. Accordingly, due to their higher polarity, aromatic solvents are more likely to be bulkier relative to aliphatic solvents to achieve comparable adsorption of a DMBP isomer.

The kinetic diameters of various solvents of relevance to the present disclosure are shown in Table 2 below (see J.

Chem. Soc., Faraday Trans., 1996, 92, 2499-2502 and J. Phys. Chem, 1996, 100, 7676-7679).

TABLE 2

| Solvent | Kinetic Diameter (Å) |
|---|---|
| iso-octane | 6.2 |
| tri-isopropyl benzene | 8.5 |
| toluene | 5.9 |
| p-xylene | 5.9 |
| m-xylene | 6.8 |
| mesitylene | 7.5 |

In some embodiments the solvent comprises a saturated organic solvent wherein the kinetic diameter of the solvent is greater than about 4.5 Å, or greater than about 5.0 Å, or greater than about 5.5 Å, or greater than about 6.0 Å.

In some embodiments the solvent comprises an aromatic organic solvent wherein the kinetic diameter of the solvent is greater than about 6.0 Å, or greater than about 6.5 Å, or greater than about 7.0 Å, or greater than about 7.5 Å.

In one embodiment the process comprises an adsorptive separation which separates 3,3'-DMBP from a mixture comprising two or more of 3,3'-DMBP, 3,4'-DMBP and 4,4'-DMBP, wherein the adsorbent comprises at least one zeolite, said zeolite comprising one or more alkali metal cations, one or more alkaline earth cations or combinations thereof, said metal cations being in the +1 or +2 oxidation states.

In another embodiment the process comprises an adsorptive separation which separates 3,3'-DMBP from a mixture comprising two or more of 3,3'-DMBP, 3,4'-DMBP and 4,4'-DMBP, wherein the adsorbent comprises at least one zeolite, said zeolite comprising barium cations.

In another embodiment the process comprises an adsorptive separation which separates 3,3'-DMBP from a mixture comprising two or more of 3,3'-DMBP, 3,4'-DMBP and 4,4'-DMBP, wherein the adsorbent comprises at least one zeolite, wherein said zeolite comprises barium cations and wherein the solvent comprises iso-octane.

In one embodiment the process comprises an adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising one or more alkali metal cations, one or more alkaline earth cations or combinations thereof, said metal cations being in the +1 or +2 oxidation states.

In another embodiment the process comprises and adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising potassium cations.

In another embodiment the process comprises an adsorptive separation which separates 3,4'-DMBP from a mixture comprising two or more of 3,3'-DMBP, 3,4'-DMBP and 4,4'-DMBP, wherein the adsorbent comprises at least one zeolite, said zeolite comprising potassium cations and wherein the solvent comprises 1,3,5-trimethylbenzene.

In one embodiment the process comprises an adsorptive separation which separates 4,4'-DMBP from a mixture comprising two or more of 3,3'-DMBP, 3,4'-DMBP and 4,4'-DMBP, wherein the adsorbent comprises at least one zeolite, said zeolite comprising one or more alkali metal cations, one or more alkaline earth cations or combinations thereof, said metal cations being in the +1 or +2 oxidation states.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises one or more zeolites, said zeolite comprising cesium cations.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises at least one zeolite, said zeolite comprising cesium cations and wherein the solvent comprises iso-octane.

In another embodiment the process comprises an adsorptive separation which separates 4,4'-DMBP from a mixture comprising two or more of 3,3'-DMBP, 3,4'-DMBP and 4,4'-DMBP wherein the adsorbent comprises at least one zeolite, said zeolite comprising a Beta zeolite and potassium cations.

In some embodiments the processes disclosed herein comprise separating 4,4'-DMBP from a mixture comprising two or more of 3,3'-DMBP, 3,4'-DMBP and 4,4'-DMBP.

In one embodiment the process comprises separating 4,4'-DMBP from a mixture comprising two or more of 3,3'-DMBP, 3,4'-DMBP and 4,4'-DMBP, wherein the zeolite has a largest diffuse along dimension of at least about 4 Angstroms (Å).

In one embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the solvent is a saturated organic solvent having a kinetic diameter greater than about 4.5 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the solvent is an aromatic organic solvent having a kinetic diameter greater than about 6.0 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), and wherein the average crystallite size of the zeolite is from about 10 to about 100 nm.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent is a saturated organic solvent having a kinetic diameter greater than about 4.5 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent is a an aromatic organic solvent having a kinetic diameter greater than about 6.0 Å.

In another embodiment the process comprises separating 4,4'-DMBP from a mixture comprising 3,3'-DMBP, 3,4'-DMBP and 4,4'-DMBP, wherein the zeolite has a largest diffuse along dimension of at least about 4 Angstroms (Å), wherein the average crystallite size of the zeolite is from about 10 to about 100 nm, and wherein the solvent comprises iso-octane, m-xylene, 1,2,4-trimethylbenzene, 1,3,5-trimethylbenzene, 1,4-diisopropylbenzene, 3,3'-DMBP, 1,3,5-triisopropylbenzene or combinations thereof.

In some embodiments the solvent heat of adsorption is less than a DMBP isomer heat of adsorption.

In some embodiments mixtures of solvents may be utilized to facilitate adsorptive separation of the DMBP isomers. In other embodiments solvent gradients may be utilized to improve separation.

In other embodiments two different adsorbents which have different adsorption characteristics for the three DMBP isomers may be utilized. For example, two different adsorbents in series operation. These separations may be performed in the presence of the same or different solvents.

For example, a first selective adsorption may preferentially adsorb one of the 3,3'-, 3,4'- or 4,4'-dimethyl biphenyl isomers in the presence of a first solvent and a second selective adsorption may preferentially adsorb one of the 3,3'-, 3,4'- or 4,4'-dimethyl biphenyl isomers not preferentially adsorbed in the first selective adsorption and in the presence of a second solvent which may be the same or different to the first solvent.

A first selective adsorption may preferentially adsorb two of the 3,3'-, 3,4'- or 4,4'-dimethyl biphenyl isomers in the presence of a first solvent and after desorption of these isomers a second selective adsorption may preferentially adsorb one of them, and in the presence of a second solvent which may be the same or different to the first solvent.

Accordingly, the use of two different adsorbents either in the presence of the same or different solvents provides a process for separating a mixture of the three DMBP isomers into pure components.

In some embodiments, the solvent or solvents used in the adsorptive separations may have a boiling point that is substantially lower than those of the DMBP isomers so as to facilitate separation of the solvents from the DMPB isomers by, for example, fractional distillation. In other embodiments a solvent of higher boiling point than those of the DMBP isomers may be utilized. Both solvents of higher and lower boiling points to those of the DMBP isomers may be utilized. In some embodiments the difference between the boiling point of the solvent or solvents and the boiling point of any one of the 3,3'-DMBP, 3,4'-DMBP and 4,4'-DMBP isomers is greater than 100° C., or greater than 75° C., or greater than 50° C., or greater than 25° C.

The person of ordinary skill in the art will appreciate that through selection of zeolite adsorbent combinations, separation of all three of 3,3'-DMBP, 3,4'-DMBP and 4,4'-DMBP may be achieved.

The processes of the present disclosure may afford pure, substantially pure or enriched individual DMBP isomers. Purities of 3,3'-DMBP, 3,4'-DMBP and 4,4'-DMBP may, independently, be greater that about 90 wt. %, or greater than about 95 wt. %, or greater than about 96 wt. %, or greater than about 97 wt. % or greater than about 98 wt. %, or greater than about 99 wt. % or greater than about 99.5 wt. % or greater than about 99.9 wt. %.

The adsorptive separations may be performed over a wide range of temperatures. Preferably the temperature is above about 20° C., more preferably above 115 C. The temperature may be between about 20° C. and about 300° C., or between about 20° C. and about 250° C., or between about 20° C. and about 200° C.

The adsorptive separations may be performed in batch or continuous mode.

The contact time between the adsorbent and the dimethyl biphenyl isomer mixture may be between a few seconds and several hours, or between a few minutes and several hours, or between about 0.5 hours and about 10 hours, or between about 0.5 hours and about 5 hours.

DETAILED DESCRIPTION OF THE EMBODIMENTS

Figure 1:
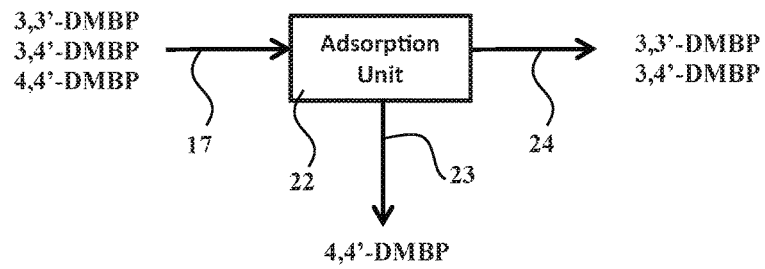
FIG. 1 is a flow diagram of a process for producing isomerically pure DMBP isomers from a mixture comprising the isomers according to one embodiment of the present disclosure.

Before the present processes are disclosed and described, it is to be understood that unless otherwise indicated this disclosure is not limited to specific compositions, components, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms 'a', 'an' and 'the' include plural referents unless otherwise specified. Thus, for example, reference to 'an alkaline earth' may include more than one alkaline earth, and the like.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

Described herein are advantageous processes for producing and separating 3,3'-, 3,4'- and 4,4'-DMBP isomers. In particular, the present disclosure provides processes for separating the dimethyl biphenyl isomers 3,3'-, 3,4'- and 4,4'-DMBP wherein the separation processes comprise at least one selective adsorption. Such separation processes may be integrated with DMBP production processes to provide processes which yield isomerically pure or substantially isomerically pure streams of each of 3,3'-, 3,4' or 4,4'-DMBP isomers. The separations may be facilitated by selective adsorption, particularly with zeolites or zeolite analogues.

Production of Dimethyl-Substituted Biphenyl Compounds from Toluene or Benzene

Exemplary production methods for dimethyl biphenyl compounds are disclosed in WO 2015/112252 the entire contents of which are incorporated by reference herein.

In one embodiment the feed employed in the presently disclosed process comprises toluene, which is initially converted to (methylcyclohexyl)toluenes by reaction with hydrogen over a hydroalkylation catalyst.

At least a portion of the hydroalkylation reaction effluent, comprising (methylcyclohexyl)toluenes, is then dehydrogenated to convert the (methylcyclohexyl)toluenes to the corresponding dimethyl biphenyl compounds.

The product of the dehydrogenation step comprises dimethyl biphenyl compounds in which the concentration of the 3,3'-, 3,4'- and 4,4' isomers is at least 50 wt %, or at least 60 wt %, or at least 70 wt % based on the total weight of dimethyl biphenyl compounds. Typically, the concentration of the 2,X'-dimethylbiphenyl isomers in the dehydrogenation product is less than 50 wt %, or less than 30 wt %, or from 5 to 25 wt % based on the total weight of dimethyl biphenyl compounds.

In other embodiments, the present process for producing dimethyl biphenyl compounds employs benzene as the feed and comprises initially converting the benzene to biphenyl. For example, benzene can be converted directly to biphenyl by reaction with oxygen over an oxidative coupling catalyst.

Alternatively, benzene can be converted to biphenyl by hydroalkylation to cyclohexylbenzene.

In either case, the biphenyl product of the oxidative coupling step or the hydroalkylation/dehydrogenation sequence is then methylated, for example with methanol, to produce dimethyl biphenyl.

Typically, the methylated product will contain from 50 to 100 wt % of 3,3'-, 3,4'- and 4,4' dimethyl biphenyl isomers and from 0 to 50 wt % of 2,X' (where X is 2, 3 or 4)-dimethyl biphenyl isomers based on the total weight of dimethyl biphenyl compounds in the methylation product.

Separation of 3,3', 3,4' and 4,4'-Dimethyl Biphenyl Isomers

Depending on the intended use of the dimethyl biphenyl isomer, it is desirable to provide a simple and effective method of separating and recovering each of the 3,3', 3,4' and 4,4' dimethyl biphenyl isomers and, in some embodiments, mixtures of two isomers. In addition, it may be desirable to convert some or all the remaining 2,X' (where X is 2, 3 or 4) dimethyl biphenyl isomers into the more desirable 3,Y' (where Y' is 3' or 4') and 4,4' dimethyl biphenyl isomers.

Irrespective of the process used, the raw dimethyl biphenyl product from the production sequences described herein will contain unreacted components and by-products in addition to a mixture of dimethyl biphenyl isomers. For example, where the initial feed comprises toluene and the production sequence involves hydroalkylation to MCHT and dehydrogenation of the MCHT, the raw dimethyl biphenyl product will tend to contain residual toluene and MCHT and by-products including hydrogen, methylcyclohexane dimethylcyclohexylbenzene, and heavy hydrocarbons in addition to the target dimethyl biphenyl isomers. Thus, in some embodiments, prior to any separation of the dimethyl biphenyl isomers, the raw product of the MCHT dehydrogenation is subjected to an initial separation to remove at least part of the residues and by-products with significantly different boiling points from the dimethyl biphenyl isomers. For example, the hydrogen by-product can be removed and recycled to the hydroalkylation and/or MCHT dehydrogenation steps, while residual toluene and methylcyclohexane by-product can be removed and recycled to the hydroalkylation step. Similarly, part of the heavy components can be removed in an initial separation and can be recovered for use as a fuel or can be reacted with toluene over a transalkylation catalyst to convert some of the dialkylate to additional MCHT. A suitable initial separation can be achieved by one or more distillations.

Table 3 depicts the structures of various components that the raw product of MHCT dehydrogenation may comprise in addition to 3,3'-DMBP, 3,4'-DMBP and 4,4'-DMBP. As will be appreciated, numerous regioisomers of the components are possible.

TABLE 3

| Structure | Name |
|---|---|
| DMBCHs | dimethyl bicyclohexanes |
| 1,X'-MCHTs | 1-methylcyclohexyl toluenes |
| CPTs | ethyl or dimethyl cyclopentyl toluenes |
| 2,X'-MCHTs | 2-methylcyclohexyl toluenes |
| 3,X'-MCHTs | 3-methylcyclohexyl toluenes |
| 4,X'-MCHTs | 4-methylcyclohexyl toluenes |
| CPDTs | cyclopentadienyl toluenes |
| 2,2'-DMBP | 2,2-dimethyl biphenyl |
| 2,3'-DMBP | 2,3-dimethyl biphenyl |
| 2,4'-DMBP | 2,4-dimethyl biphenyl |

Conversion of 2,X'-Dimethyl Biphenyl Isomers

In some embodiments, part or all of the 2,X'-dimethyl biphenyl (DMBP) isomers in the second stream described above, can be processed to increase the concentration of 3,3'-, 3,4'- and 4,4'-dimethyl biphenyl (DMBP) in the second stream. One suitable process comprises a combination of hydrogenation of the DMBP back to MCHT, followed by transalkylation of the MCHT with toluene and then dehydrogenation of the transalkylation product back to DMBP. In some embodiments the hydrogenation unit and transalkylation unit can be combined as a single reactor. Such a process is described in WO 2015/191289 the entire contents of which are incorporated by reference herein. In particular, it is found that steric issues favor the transalkylation of 1-methyl-2-(X-methylcyclohexyl)benzene (where X=2, 3 or 4) with toluene to produce 1-methyl-Y—(X-methylcyclohexyl)benzene (where Y=3 or 4 and X is the same position as the feed).

Particularly, where the DMBP is produced via hydroalkylation of toluene, this process of increasing 3,3'-, 3,4' and 4,4' DMBP concentration can be achieved by recycling the hydrogenated second stream to the hydroalkylation/dehydrogenation sequence.

Selective Adsorbents

In some embodiments the adsorbent of the present disclosure is a zeolite or zeolite analogue.

In some embodiments the adsorbent is at least one zeolite, wherein said zeolite has a largest diffuse along dimension of at least about 4 Angstroms (Å).

In other embodiments the adsorbent is at least one zeolite, wherein said zeolite comprises one or more metal cations in the +1 or +2 oxidation states.

In other embodiments the adsorbent is at least one zeolite, wherein said zeolite has a largest diffuse along dimension of at least about 4 Angstroms (Å) and wherein said zeolite comprises one or more metal cations in the +1 or +2 oxidation states.

Preferably the largest diffuse along dimension of the zeolite is at least about 4.5 Å, or at least about 5.0 Å, or at least about 5.5 Å, or at least about 6.0 Å, or at least about 6.5 Å, or at least about 7.0 Å.

Preferably the largest diffuse along dimension of the zeolite is between about 4.0 Å and about 8.0 Å, or between about 4.5 Å and about 8.0 Å, or between about 5.0 Å and about 8.0 Å, or between about 5.5 Å and about 8.0 Å, or between about 6.0 Å and about 8.0 Å, or between about 6.5 Å and about 8.0 Å.

Numerous zeolite structural types are useful as selective adsorbents in the present processes, for example, BEA, FAU, MFI, MEL, MTW, MOR, LTL, EMT, FER, MAZ, MEI, TON, MWW, EUO, MFS, IMF, MRE, ITN, MSE, MTT and IWV.

Preferred zeolites comprise a 12-ring zeolite, an 11-ring zeolite or a 10-ring zeolite.

In some embodiments the zeolite comprises one or more alkali metal cations, alkaline earth metal cations, transition metal cations, rare earth metal cations or combinations thereof. Preferred cations are alkali metal or alkaline earth cations.

The zeolite may comprise one or more metal cations, wherein the ionic radius of the metal cation is between about 0.8 Å and about 2.0 Å.

The molar ratio of metal cations relative to aluminum in the zeolite may be between about 0.01 and about 2.0, or between about 0.05 and about 1.5, or between about 0.1 and about 1.0.

It has been discovered that particular metal cations improve the separation of particular DMBP isomers. The separation may be based on preferential adsorption of one or more DMBP isomers within the pores of the zeolite.

It has also been discovered that the crystallite size of the zeolite may improve the adsorptive ability for DMBP isomers.

The average crystallite size of the zeolite may be less than about 5000 nm, or less than about 2000 nm, or less than about 1000 nm, or less than about 500 nm, or less than about 200 nm, or less than about 100 nm, or less than about 50 nm.

The average crystallite size of the zeolite may be from about 1 to about 5000 nm, or from about 1 to about 2000 nm, or from about 1 to about 1000 nm, or from about 5 to about 500 nm, or from about 10 to about 100 nm.

In some embodiments, the zeolite is substantially metal cation free.

Both the natural and synthetic zeolites may be used as adsorbents in the processes of the present disclosure. A zeolite encompassed by the present disclosure for use as an adsorbent includes aluminosilicate cage structures in which the alumina and silica tetrahedra are intimately connected with each other in an open three-dimensional crystalline network. The tetrahedra are cross-linked by the sharing of oxygen atoms. The spaces between the tetrahedra are occupied by water molecules prior to dehydration. Subsequent partial or total dehydration results in crystals interlaced with channels of molecular dimensions. In the hydrated form, the crystalline aluminosilicates may be represented by the formula

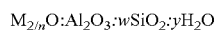

$$M_{2/n}O:Al_2O_3:wSiO_2:yH_2O$$

where M is a metal cation which balances the electrovalence of the tetrahedra, n represents the valence of the metal cation, w represents the mols of $SiO_2$ and Y, the mols of water. The metal cations may be any one of a number of cations such as for example the alkali metal cations or the alkaline earth cations or other selected metal cations.

Zeolites which find use as adsorbents in the process of the present disclosure may possess relatively well-defined pore structure. The exact zeolite type may be generally referred to by the particular silica-alumina ratio and the pore dimensions of the cage structures. For example, the faujasites are commonly represented as type X and type Y aluminosilicates and are defined by their varying silica to alumina ratios.

Cationic exchange or base exchange methods are generally known to those familiar with the field of zeolite production and are generally performed by contacting a zeolite with an aqueous solution of soluble salts of the cation or cations desired to be exchanged on the zeolite. The desired degree of cation exchange is allowed to take place before the zeolite is removed from the aqueous solution and dried to a desired water content. It is contemplated that in cationic exchange or base exchange methods that the cation exchange may take place using individual solutions of desired cations to be placed on the zeolite or can use exchange solutions containing mixtures of the cations which are desired to be exchanged onto the zeolite.

Preferably the metal cations are selected from the group consisting of potassium, rubidium, cesium, barium, copper, silver, lithium, sodium, beryllium, magnesium, calcium, strontium, cadmium, cobalt, nickel, manganese and zinc and combinations thereof.

In one preferred embodiment of the adsorptive separation process herein disclosed when the separation of 3,3'-DMBP from its isomeric mixtures is desired improved results can be attained by choosing a potassium or barium cation or mixtures thereof and performing the separation in iso-octane solvent. This system displays a pronounced selectivity for the adsorption of 3,3'-DMBP as compared to 3,4'-DMBP and 4,4'-DMBP.

In another preferred embodiment of the adsorptive separation process herein disclosed when the separation of 3,4'-DMBP from its isomeric mixtures is desired improved results can be attained by choosing a cesium cation and performing the separation in mesitylene. This system displays a pronounced selectivity for the adsorption of both 3,3'-DMBP and 4,4'-DMBP compared to 3,4'-DMBP.

In another preferred embodiment of the adsorptive separation process herein disclosed when the preferred adsorption of 4,4'-DMBP from its isomeric mixtures is desired improved results can be attained by choosing a potassium cation and performing the separation in iso-octane. This system displays a pronounced selectivity for the adsorption of 4,4'-DMBP as compared to 3,3'-DMBP and 3,4'-DMBP.

In separating the 3,3'-DMBP isomer in the process of this disclosure a bed of solid adsorbent may be contacted with a feed mixture, the 3,3'-DMBP is preferentially adsorbed on the adsorbent, the unadsorbed or raffinate mixture is removed from the adsorbent bed, and the adsorbed 3,3'-DMBP is removed from the solid adsorbent.

In separating the 4,4'-DMBP isomer in the process of this disclosure a bed of solid adsorbent may be contacted with a feed mixture, the 4,4'-DMBP is preferentially adsorbed on the adsorbent, the unadsorbed or raffinate mixture is removed from the adsorbent bed, and the adsorbed 4,4'-DMBP is removed from the solid adsorbent.

In separating the 3,4'-DMBP isomer in the process of this disclosure a bed of solid adsorbent may be contacted with a feed mixture, the 3,3'-DMBP and 4,4'-DMBP are preferentially adsorbed on the adsorbent, the unadsorbed 3,4-DMBP is removed from the adsorbent bed, and the adsorbed 3,3'-DMBP and 4,4'-DMBP removed from the solid adsorbent.

The solvent used in the adsorptive separations of the processes of the present disclosure should be a material that is separable from the mixture that is fed to the solid adsorbent. In desorbing the adsorbed component of the feed, both the solvent and the desorbed feed component are removed from the adsorbent bed as a mixture, and without a method of separation of these two materials the purity of the adsorbed component of the feed would not be very high. Therefore, it is contemplated that a solvent that is of a different boiling range than the feed mixture fed to the solid adsorbent be used in this separation process. The use of a solvent of a differing boiling range would allow fractionation or other separation methods to be used to separate the selectively adsorbed feed component as a relatively pure product stream and allow recovery of the solvent for possible recycle in the process.

Solvents which can used in the process of the present disclosure include, for example, iso-octane and mesitylene. Iso-octane and mesitylene have boiling points of 99 and 165° C. respectively, whereas 3,3'-DMBP, which is the lowest boiling DMBP isomer, boils at around 289° C.

The adsorbent can be contained in a single vessel where, through programmed flow into and out of the vessel, a separation of a desired DMBP isomer is effected. Swing bed operational techniques where a series of adsorbent vessels are available or simulated moving bed countercurrent operations may be used. In the latter method of operations the selection of a suitable solvent requires that it be capable of readily displacing a particular adsorbed DMBP isomer from the adsorbent.

Embodiments of the present disclosure are illustrated through numerous exemplary process configurations which improve the efficiency of production and separation of 3,3'-, 3,4', and 4,4'-DMBP isomers.

Each exemplary process configuration takes a mixture of 3,3'-, 3,4'-, and 4,4'-DMBP from a distillation unit and isolates a desired quantity of isomerically pure product. The initial isomer ratio is defined by the catalytic steps that feed the distillation unit and the feed may also comprise amounts of 2,X'-DMBPs (2,2'-, 2,3'-, and 2,4'-DMBP). The present disclosure describes processes in which two or all three of the individual isomers may be isolated using two separation steps. Process configuration choice may be dependent on the relative amounts of each isomer in the stream to be separated, market requirements at any particular time and the performance of the adsorbents used in these processes. Table 4 summarizes 22 different process embodiments utilizing at least one adsorptive separation to separate 3,3'-, 3,4'-, and 4,4'-DMBP isomers.

In some embodiments two adsorptive separations are used. The first adsorptive separation isolates one pure DMBP isomer from a mixture of the other two isomers. The second unit then separates the mixture of the other two isomers into two isomerically pure products.

In some embodiments excess production of any of the isomers can be converted to a desired isomer by recycling the excess back to either a hydrogenation/transalkylation unit or an isomerization unit. For example, configuration 1.1 in Table 4 illustrates the first product as being isomerically pure 4,4'-DMBP isolated in a first adsorption and both 3,4'-DMBP and 3,3'-DMBP as second and third products isolated in a second adsorption. Depending on the relative amounts of 3,3'- and 3,4'-DMBP that are desired, the process may be modified to produce 3,3'-DMBP as isolated product 2 and recycle excess 3,4'-DMBP that is produced. This scenario is shown as configuration 1.2 in Table 4. Additional configurations 1.3 through 1.6 offer the option to isolate 3,4'- or 3,3'-DMBP in the first step.

In some embodiments, if 3,4'-DMBP, for example, is present in the highest concentration in the isomer mixture and it has the largest market potential at a particular time, configurations 1.3 or 1.4 may be desirable and some isomerically pure 3,3'-DMBP and 4,4'-DMBP may be produced in a second separation. Overall, the size and energy input would be smaller if the 3,4'-DMBP is removed in the first step. It will be appreciated that the efficiency of the adsorbent for each particular separation may affect the choice of configuration.

TABLE 4

| Configuration | Primary Separation Technology | Isolated Product 1 | Feed to 2nd step | Secondary Separation Technology | Isolated Product 2 | Isolated Product 3 | Method of Converting Excess |
|---|---|---|---|---|---|---|---|
| 1.1 | Adsorption | 4, 4' | 3, 3' + 3, 4' | Adsorption | 3, 4' | 3, 3' | HYD/TA |
| 1.2 | Adsorption | 4, 4' | 3, 3' + 3, 4' | Adsorption | 3, 3' | 3, 4' | HYD/TA |
| 1.3 | Adsorption | 3, 4' | 3, 3' + 4, 4' | Adsorption | 4, 4' | 3, 3' | HYD/TA |
| 1.4 | Adsorption | 3, 4' | 3, 3' + 4, 4' | Adsorption | 3, 3' | 4, 4' | HYD/TA |
| 1.5 | Adsorption | 3, 3' | 3, 4' + 4, 4' | Adsorption | 4, 4' | 3, 4' | HYD/TA |
| 1.6 | Adsorption | 3, 3' | 3, 4' + 4, 4' | Adsorption | 3, 4' | 4, 4' | HYD/TA |
| 2.1 | Adsorption | 4, 4' | 3, 3' + 3, 4' | Adsorption | 3, 4' | 3, 3' | Isomerization |
| 2.2 | Adsorption | 4, 4' | 3, 3' + 3, 4' | Adsorption | 3, 3' | 3, 4' | Isomerization |
| 2.3 | Adsorption | 3, 4' | 3, 3' + 4, 4' | Adsorption | 4, 4' | 3, 3' | Isomerization |
| 2.4 | Adsorption | 3, 4' | 3, 3' + 4, 4' | Adsorption | 3, 3' | 4, 4' | Isomerization |
| 2.5 | Adsorption | 3, 3' | 3, 4' + 4, 4' | Adsorption | 4, 4' | 3, 4' | Isomerization |
| 2.6 | Adsorption | 3, 3' | 3, 4' + 4, 4' | Adsorption | 3, 4' | 4, 4' | Isomerization |
| 3.1 | Adsorption | 4, 4' | 3, 3' + 3, 4' | Crystallization | 3, 4' | Mixed isomers | HYD/TA |
| 3.2 | Adsorption | 3, 4' | 3, 3' + 4, 4' | Crystallization | 4, 4' | Mixed isomers | HYD/TA |
| 3.3 | Adsorption | 3, 3' | 3, 4' + 4, 4' | Crystallization | 4, 4' | Mixed isomers | HYD/TA |
| 4.1 | Adsorption | 4, 4' | 3, 3' + 3, 4' | Crystallization | 3, 4' | Mixed isomers | Isomerization |
| 4.2 | Adsorption | 3, 4' | 3, 3' + 4, 4' | Crystallization | 4, 4' | Mixed isomers | Isomerization |
| 4.3 | Adsorption | 3, 3' | 3, 4' + 4, 4' | Crystallization | 4, 4' | Mixed isomers | Isomerization |
| 5.1 | Crystallization | 4, 4' | 3, 3' + 3, 4' + 4, 4' | Adsorption | 3, 4' | Mixed isomers | HYD/TA |
| 5.2 | Crystallization | 4, 4' | 3, 3' + 3, 4' + 4, 4' | Adsorption | 3, 3' | Mixed isomers | HYD/TA |
| 6.1 | Crystallization | 4, 4' | 3, 3' + 3, 4' + 4, 4' | Adsorption | 3, 4' | Mixed isomers | Isomerization |
| 6.2 | Crystallization | 4, 4' | 3, 3' + 3, 4' + 4, 4' | Adsorption | 3, 3' | Mixed isomers | Isomerization |

In another embodiment an alternative method of handling excess production of isolated products 2 and 3, when isolated product 1 is the main production target, is to utilize an isomerization unit to convert products 2 and 3 using, for example, acid-based catalysis to a mixture of dimethyl biphenyls. Configurations 2.1 to 2.6 are similar to 1.1 to 1.6 with an added isomerization unit to recycle the excess of the less desired isomers. Using configuration 2.1 as an example, a portion of the unneeded 3,4'- and 3,3'-DMBP may be diverted directly to an isomerization unit. The output from isomerization may be optionally returned to the first adsorption unit. This option may be utilized if isomerization is optimized to minimize by-product formation and/or if the adsorption is optimized to retain the 2,X'-DMBP in the effluent that ultimately goes back to isomerization.

The choice between hydrogenation/transalkylation or isomerization to perform the conversion to a particularly desired isomer may be based on the isomer distribution produced in the initial chemical synthesis and the relative amounts of products that are desired. For example, if relatively small amounts of DMBP are being isomerized, it may be desirable to send the excess to hydrogenation/transalkylation. But if the amount of DMBP being recycled is large, the efficiency of an acid catalyzed isomerization unit may be advantageous.

In some embodiments combining one adsorption step with one crystallization step may offer an advantage to reduce the recycle stream size and associated equipment size. This results from the ability of adsorptive separation to separate a very high percentage of the isomer, for example >99.5%, from the mixture of other isomers. This compares to crystallization that may only be used to isolate a given isomer to a concentration fixed by the eutectic point. Therefore the efficiency and cost of a process that utilizes at least one adsorptive separation may have economic advantages.

Accordingly, any of configurations 3 through 6, only allow production of two separate pure isomer products with an option to produce a mixed isomer stream that could be used in some product applications. Alternate processes that employ two crystallizers and one large distillation tower may offer the possibility of isolating two separate and pure isomeric DMBP products, but the recycle stream will always contain all of the isomers in significant concentrations and will therefore be larger in volume.

Various configurations may be employed based on the performance of the adsorbent and the ultimately desired products. Configurations 3 and 4, utilize adsorptive separation first followed by crystallization and use either hydrogenation/transalkylation or direct isomerization to convert the excess of unwanted isomers to desired isomer.

As the solubility of 4,4'-DMBP is relatively low in the mixture of isomers and because it melts at 120-123° C., it is possible to operate a crystallizer at or close to ambient temperature and produce pure 4,4'-DMBP. These physical properties allow the option to configure a process with a crystallizer before an adsorptive separation unit. However, crystallization is limited at reasonable relative concentrations of isomers to precipitation of only 4,4'-DMBP, unless laborious steps are taken to concentrate 3,4'-DMBP before a crystallizer. The present discovery that 3,3'-DMBP or 3,4'-DMBP can be isolated directly from any mixture of the three isomers thus allows the secondary adsorptive separation unit to be engineered to produce either of these products.

The disclosure will now be more particularly described with reference to the following non-limiting examples and FIGS. 1 to 26 of the accompanying drawings.

One embodiment of a process for separating a feed stream comprising 3,3'-, 3,4'- and 4,4'-DMBP isomers into a product stream pure, substantially pure, or rich in one of the isomers is illustrated in FIG. 1, in which a feed comprising the isomers is fed via line 17 to an adsorption unit 22 which preferentially adsorbs, for example, 4,4'-DMBP, which exits the adsorption unit as a stream rich in 4,4'-DMBP via line 23. The remaining 4,4'-DMBP depleted stream, which comprises 3,3'- and 3,4'-DMBP, exits the adsorption unit via line 24.

Figure 2:
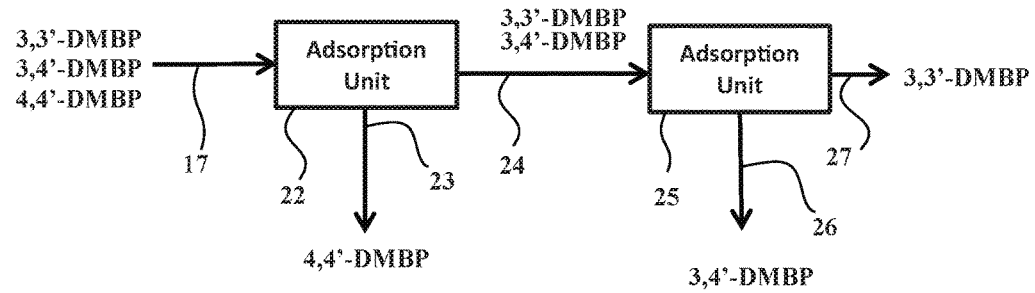
FIG. 2 is a flow diagram of a process for producing isomerically pure DMBP isomers from a mixture comprising the isomers according to one embodiment of the present disclosure.

In another embodiment FIG. 2 illustrates a process for separating a feed stream comprising 3,3'-, 3,4'- and 4,4'-DMBP isomers into product streams pure, substantially pure, or rich in each of the 3,3'-, 3,4'- and 4,4'-DMBP isomers. A feed comprising the isomers is fed via line 17 to an adsorption unit 22 which preferentially adsorbs, for example, 4,4'-DMBP, which exits the adsorption unit as a stream rich in 4,4'-DMBP via line 23. The remaining 4,4'-DMBP depleted stream, which comprises 3,3'- and 3,4'-DMBP, exits via line 24 and is subsequently fed to a second adsorption unit 25 which preferentially adsorbs, for example, 3,4'-DMBP, which exits the second adsorption unit as a stream rich in 3,4'-DMBP via line 26. The 3,3'-DMBP exits the adsorption unit via line 27.

Figure 3:
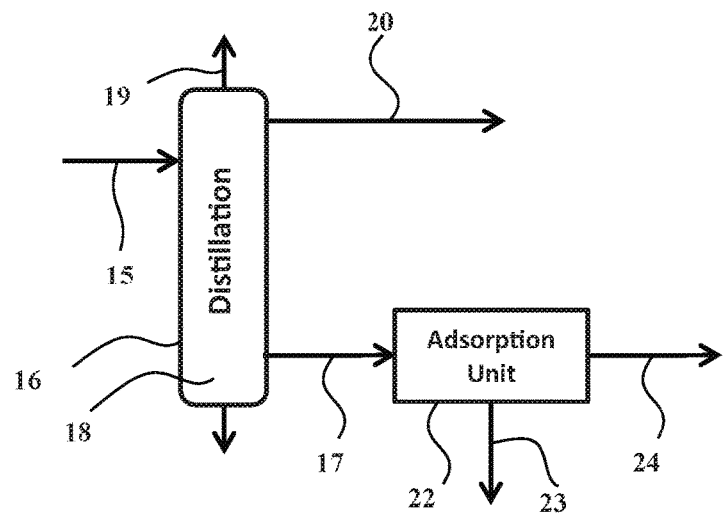
FIG. 3 is a flow diagram of a process for producing isomerically pure DMBP isomers from a mixture comprising the isomers according to one embodiment of the present disclosure.

Another embodiment of a process for separating a feed stream comprising 3,3'-, 3,4'- and 4,4'-DMBP isomers into a product stream pure, substantially pure, or rich in one of the 3,3', 3,4' and 4,4' DMBP isomers is illustrated in FIG. 3, in which a raw feed comprising the isomers is fed via line 15 to a distillation unit 16, where the 3,3', 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

The 3,3', 3,4'- and 4,4'-DMBP isomers leaving the distillation unit via line 17 are fed to an adsorption unit 22 which preferentially adsorbs, for example, 4,4'-DMBP which exits the adsorption unit as a stream rich in 4,4'-DMBP via line 23. The remaining 4,4'-DMBP depleted stream, which comprises 3,3'- and 3,4'-DMBP, exits via line 24.

Figure 4:
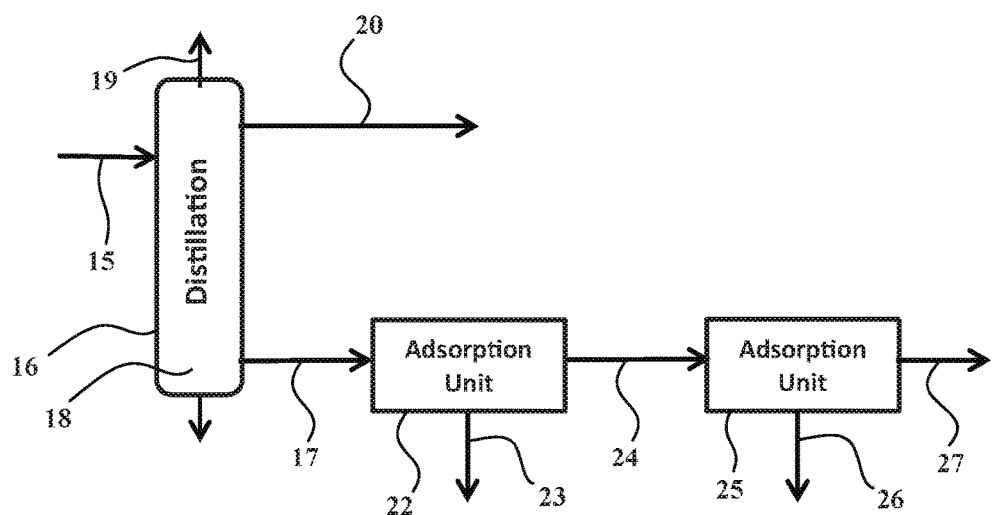
FIG. 4 is a flow diagram of a process for producing isomerically pure DMBP isomers from a mixture comprising the isomers according to one embodiment of the present disclosure.

In another embodiment FIG. 4 illustrates a process for separating a feed stream comprising 3,3'-, 3,4'- and 4,4'-DMBP isomers into product streams pure, substantially pure, or rich in each of the 3,3'-, 3,4'- and 4,4'-DMBP isomers. A feed comprising the isomers is fed via line 15 to a distillation unit 16, where the 3,3', 3,4'- and 4,4'-DMBP isomers are separated and removed via line 17. More volatile unreacted MCHT and 2,X'-DMBP isomers are separated and removed via line 20. A heavy fraction is removed via line 18 and a light fraction via line 19.

The 3,3', 3,4'- and 4,4'-DMBP isomers leaving the distillation unit are fed via line 17 to an adsorption unit 22 which preferentially adsorbs, for example, 4,4'-DMBP, which exits the adsorption unit as a stream rich in 4,4'-DMBP via line 23. The remaining 4,4'-DMBP depleted stream, which comprises 3,3'- and 3,4'-DMBP, exits via line 24 and is subsequently fed to a second adsorption unit 25 which preferentially adsorbs, for example, 3,4'-DMBP, which exits the second adsorption unit as a stream rich in 3,4'-DMBP via line 26. The 3,3'-DMBP exits the adsorption unit via line 27.

Figure 5:
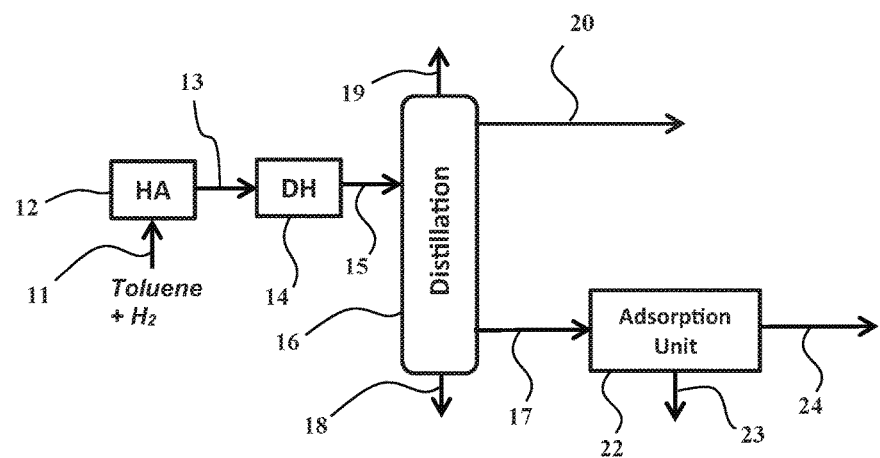
FIG. 5 is a flow diagram of a process for producing isomerically pure DMBP isomers from toluene according to one embodiment of the present disclosure.

An embodiment of a process for producing separate product streams pure, substantially pure, or rich in each of the 3,3', 3,4' and 4,4' DMBP isomers from a toluene-containing feed is illustrated in FIG. 5, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17. More volatile unreacted MCHT and 2,X'-DMBP isomers are separated and removed via line 20. A heavy fraction removed via line 18 and a light fraction via line 19.

The raw DMBP-containing product leaving the distillation unit is then fed via line 17 to a first adsorption unit 22 which preferentially adsorbs, for example, 4,4'-DMBP, which exits the adsorption unit as a stream rich in 4,4'-DMBP via line 23. The remaining 4,4'-DMBP depleted stream which comprises 3,3'- and 3,4'-DMBP exits via line 24.

Figure 6:
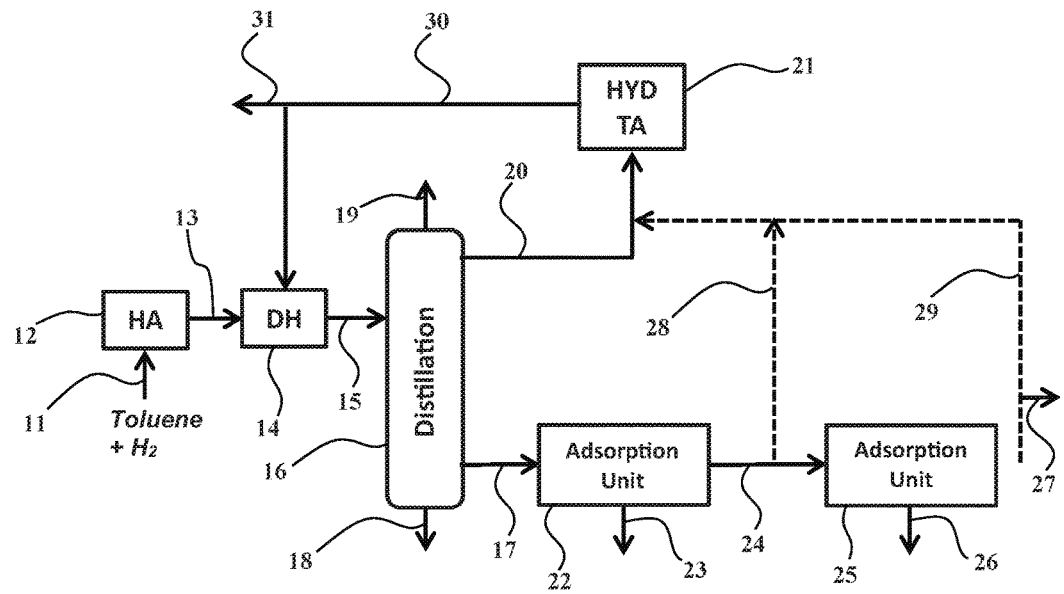
FIG. 6 is a flow diagram of a process for producing isomerically pure DMBP isomers from toluene according to one embodiment of the present disclosure.

Another embodiment of a process for producing separate product streams pure, substantially pure, or rich in each of the 3,3', 3,4' and 4,4' DMBP isomers from a toluene-containing feed is illustrated in FIG. 6, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17, a heavy fraction removed via line 18 and a light fraction via line 19. More volatile unreacted MCHT and 2,X'-DMBP isomers are separated and removed via line 20. This mixture is feed to hydrogenation/transalkylation unit 21 to convert the 2,X'-DMBP isomers to a mixture of MCHT isomers. The effluent from the hydrogenation/transalkylation unit is fed via line 30 to the dehydrogenation unit 14 to produce DMBP isomers.

The raw DMBP-containing product leaving the distillation unit is then fed via line 17 to a first adsorption unit 22 which preferentially adsorbs 4,4'-DMBP which exits the adsorption unit as a stream rich in 4,4'-DMBP via line 23. The remaining 4,4'-DMBP depleted stream which contains 3,3'- and 3,4'-DMBP exits via line 24. The mixture of 3,3'- and 3,4'-DMBP is then fed via line 24 to a second adsorption unit 25 which separates the 3,4'-DMBP which exits via line 26 from 3,3'-DMBP which exits via line 27.

Optionally, some or all of stream 24 may be fed via line 28 to hydrogenation/transalkylation unit 21, to convert the 3,3'- and 3,4'-DMBP isomers to a mixture of MCHT isomers. Similarly, some or all of stream 27 comprising 3,3'-DMBP may be fed to the hydrogenation/transalkylation unit via line 29. The effluent from the hydrogenation/transalkylation unit is fed via line 30 to the dehydrogenation unit 14 to produce DMBP isomers. This embodiment affords flexibility to the process whereby the relative amounts of each of the DMBP isomers may be controlled based on market needs. Optionally, purge line 31 removes 1,X'-MHCTs and CPTs.

Figure 7:
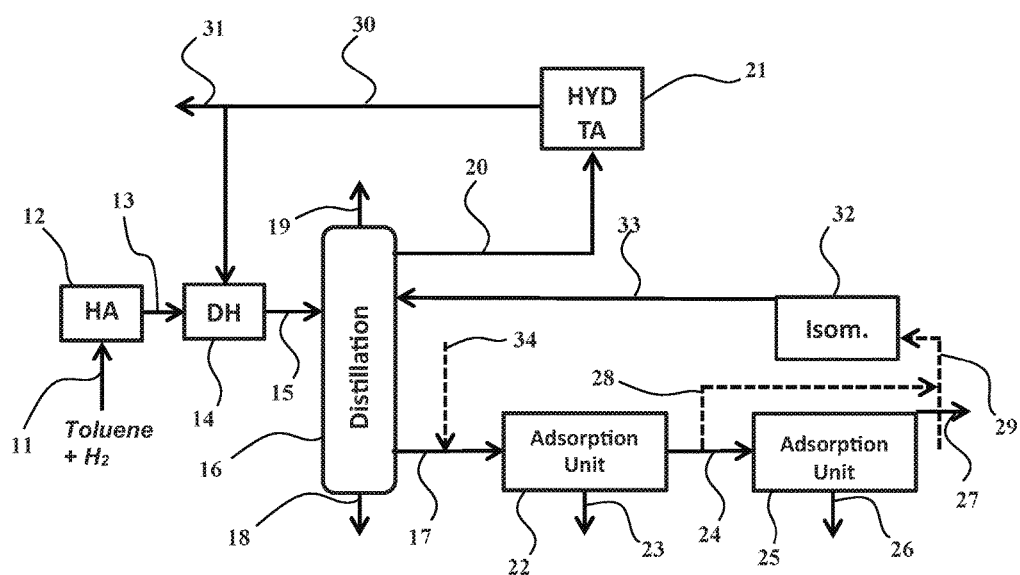
FIG. 7 is a flow diagram of a process for producing isomerically pure DMBP isomers from toluene according to one embodiment of the present disclosure.

Another embodiment of a process for producing separate product streams pure, substantially pure, or rich in each of the 3,3', 3,4' and 4,4' DMBP isomers from a toluene-containing feed is illustrated in FIG. 7, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17, a heavy fraction removed via line 18 and a light fraction via line 19. More volatile unreacted MCHT and 2,X'-DMBP isomers are separated and removed via line 20. This mixture is feed to hydrogenation/transalkylation unit 21 to convert the 2,X'-DMBP isomers to a mixture of MCHT isomers. The effluent from the hydrogenation/transalkylation unit is fed via line 30 to the dehydrogenation unit.

The raw DMBP-containing product leaving the distillation unit is then fed via line 17 to a first adsorption unit 22 which preferentially adsorbs 4,4'-DMBP which exits the adsorption unit as a stream rich in 4,4'-DMBP via line 23. The remaining 4,4'-DMBP depleted stream which contains 3,3'- and 3,4'-DMBP exits via line 24. The mixture of 3,3'- and 3,4'-DMBP is then fed via line 24 to a second adsorption unit 25 which separates the 3,4'-DMBP which exits via line 26 from 3,3'-DMBP which exits via line 27.

Optionally, some or all of stream 24 may be fed via line 28 to isomerization unit 32, which affords a mixture of DMBP isomers. Similarly, and optionally, some or all of stream 27 may be fed to the isomerization unit via line 29. The effluent from the isomerization unit is fed via line 33 to the distillation column. This affords flexibility to the process whereby the relative amounts of each of the DMBP isomers may be controlled based on market needs. Optionally, and depending on stream content, the output of the isomerization unit may be wholly or partly fed to the first adsorption unit via line 34. Optionally, purge line 31 separates 1,X'-MHCTs and CPTs.

Figure 8:
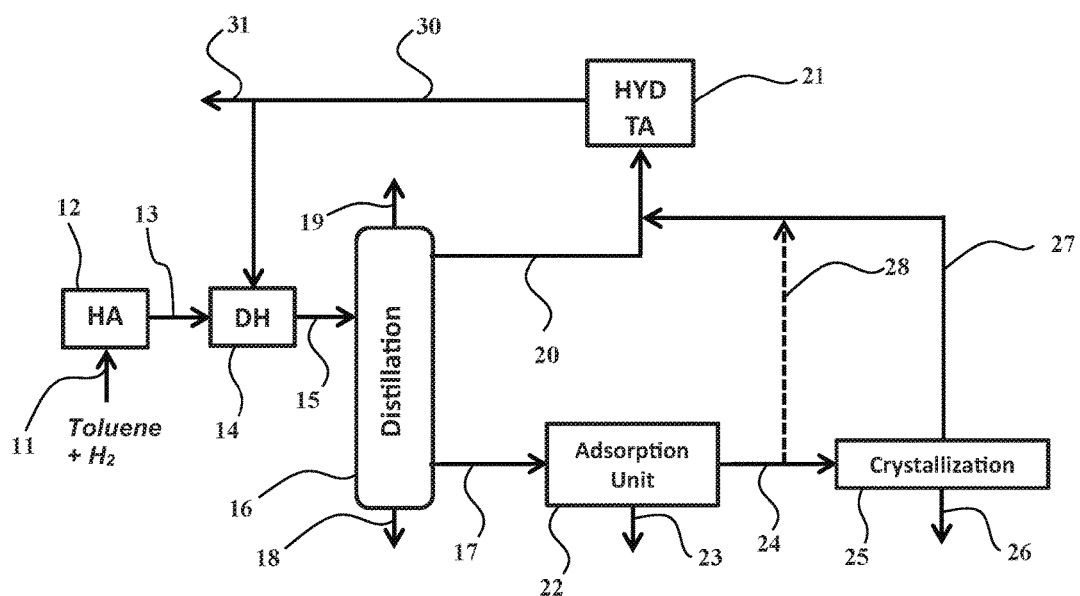
FIG. 8 is a flow diagram of a process for producing isomerically pure DMBP isomers from toluene according to one embodiment of the present disclosure.

Another embodiment of a process for producing separate product streams pure, substantially pure, or rich in each of the 3,3', 3,4' and 4,4' DMBP isomers from a toluene-containing feed is illustrated in FIG. 8, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17, a heavy fraction removed via line 18 and a light fraction via line 19. More volatile unreacted MCHT and 2,X'-DMBP isomers are separated and removed via line 20. This mixture is feed to hydrogenation/transalkylation unit 21 to convert the 2,X'-DMBP isomers to a mixture of MCHT isomers. The effluent from the hydrogenation/transalkylation unit is fed via line 30 to the dehydrogenation unit 14 to produce DMBP isomers.

The raw DMBP-containing product leaving the distillation unit is then fed via line 17 to an adsorption unit 22 which preferentially adsorbs 3,4'-DMBP which exits the adsorption unit as a stream rich in 3,4'-DMBP via line 23. The remaining 3,4'-DMBP depleted stream which contains 3,3'- and 4,4'-DMBP is exits via line 24. The mixture of 3,3'- and 4,4'-DMBP is then fed via line 24 to a crystallization unit 25 which crystallizes the 4,4'-DMBP which exits as a product via line 26. Non-crystallizing 3,3'-DMBP exits via line 27.

Optionally, some or all of stream 24 may be fed via line 28 to hydrogenation/transalkylation unit 21, to convert the 3,3'- and 4,4'-DMBP isomers to a mixture of MCHT isomers. The effluent from the hydrogenation/transalkylation reactor is fed via line 30 to the dehydrogenation unit. This affords flexibility to the process whereby the relative amounts of each of the DMBP isomers may be controlled based on market needs. Optionally, purge line 31 removes 1,X'-MHCTs and CPTs.

Figure 9:
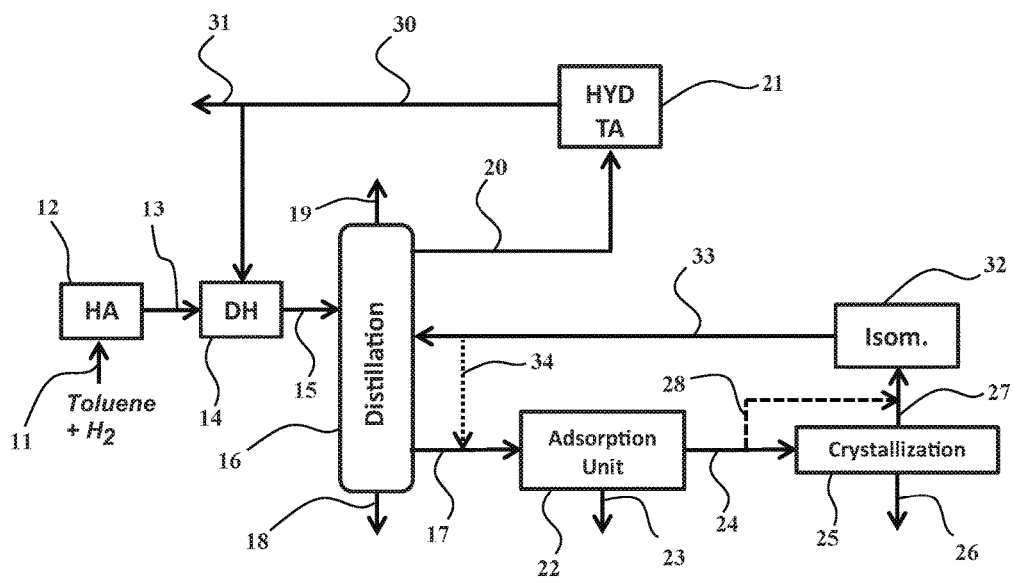
FIG. 9 is a flow diagram of a process for producing isomerically pure DMBP isomers from toluene according to one embodiment of the present disclosure.

Another embodiment of a process for producing separate product streams pure, substantially pure, or rich in each of the 3,3', 3,4' and 4,4' DMBP isomers from a toluene-containing feed is illustrated in FIG. 9, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17, a heavy fraction removed via line 18 and a light fraction via line 19. More volatile unreacted MCHT and 2,X'-DMBP isomers are separated and removed via line 20. This mixture is feed to hydrogenation/transalkylation unit 21 to convert the 2,X'-DMBP isomers to a mixture of MCHT isomers. The effluent from the hydrogenation/transalkylation unit is fed via line 30 to the dehydrogenation unit 14 to produce DMBP isomers.

The raw DMBP-containing product leaving the distillation unit is then fed via line 17 to adsorption unit 22 which preferentially adsorbs 3,4'-DMBP which exits the adsorption unit as a stream rich in 3,4'-DMBP via line 23. The remaining 3,4'-DMBP depleted stream which contains 3,3'- and 4,4'-DMBP exits via line 24. The mixture of 3,3'- and 4,4'-DMBP is then fed via line 24 to a crystallization unit 25 which crystallizes the 4,4'-DMBP which exits as a product via line 26. Non-crystallizing 3,3'-DMBP exits via line 27.

Optionally, some or all of stream 24 may be fed via line 28 to isomerization unit 32, which affords a mixture of DMBP isomers. The effluent from the isomerization unit is fed via line 33 to the distillation unit. This affords flexibility to the process whereby the relative amounts of each of the DMBP isomers may be controlled based on market needs. Optionally, and depending on stream content, the output of the isomerization unit may be wholly or partly fed to the adsorption unit via line 34. Optionally, purge line 31 separates 1,X'-MHCTs and CPTs.

Figure 10:
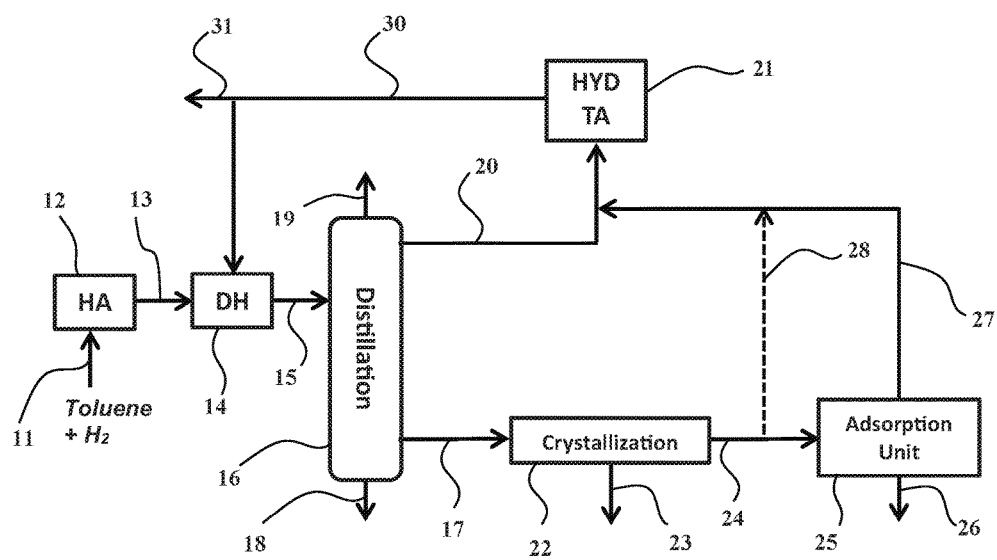
FIG. 10 is a flow diagram of a process for producing isomerically pure DMBP isomers from toluene according to one embodiment of the present disclosure.

Another embodiment of a process for producing separate product streams pure, substantially pure, or rich in each of the 3,3', 3,4' and 4,4' DMBP isomers from a toluene-containing feed is illustrated in FIG. 10, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17, a heavy fraction removed via line 18 and a light fraction via line 19. More volatile unreacted MCHT and 2,X'-DMBP isomers are separated and removed via line 20. This mixture is feed to hydrogenation/transalkylation unit 21 to convert the 2,X'-DMBP isomers to MCHT isomers.

The raw DMBP-containing product leaving the distillation unit is then fed via line 17 to crystallization unit 22 which preferentially crystallizes 4,4'-DMBP which exits the adsorption unit as pure 4,4'-DMBP via line 23. The remaining 4,4'-DMBP deficient stream and which is concentrated in 3,3'- and 3,4'-DMBP exits via line 24. The mixture of isomers is then fed via line 24 to an adsorption unit 25 which separates the 3,4'-DMBP which exits via line 26 from 3,3'- and 4,4'-DMBP which exit via line 27.

Optionally, a portion of stream 24 may be fed via line 28 to hydrogenation/transalkylation unit 21, to convert the 3,3'- and 3,4'-DMBP isomers to a mixture comprising MHCT isomers. The effluent from the hydrogenation/transalkylation unit is fed via line 30 to the dehydrogenation unit 14. This affords flexibility to the process whereby the relative amounts of each of the DMBP isomers may be controlled based on market needs. Optionally, purge line 31 removes 1,X'-MHCTs and CPTs.

Figure 11:
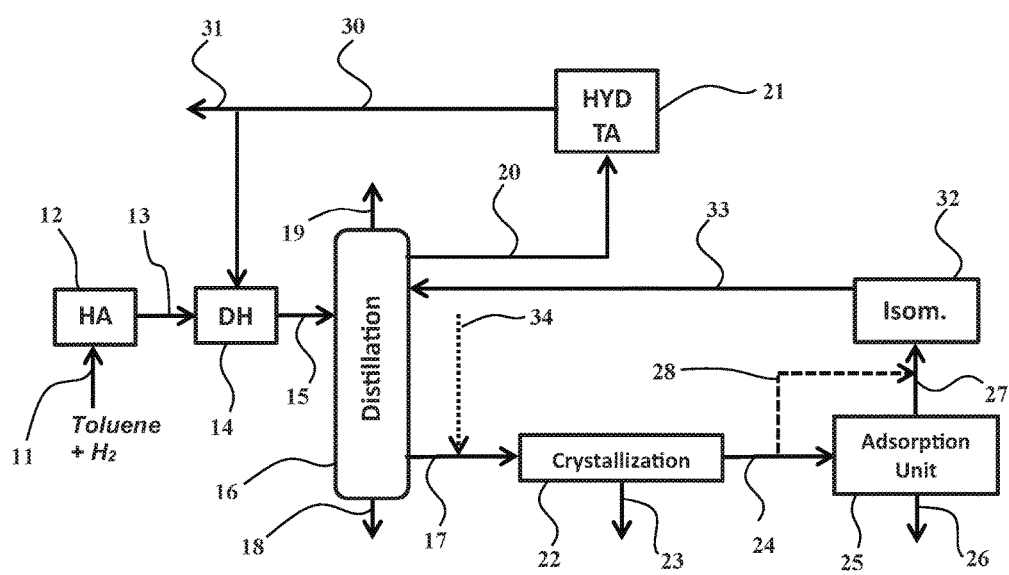
FIG. 11 is a flow diagram of a process for producing isomerically pure DMBP isomers from toluene according to one embodiment of the present disclosure.

Another embodiment of a process for producing separate product streams pure, substantially pure, or rich in each of the 3,3', 3,4' and 4,4' DMBP isomers from a toluene-containing feed is illustrated in FIG. 11, in which toluene and hydrogen are fed by a single line 11 or, if preferred by separate lines (not shown), to a hydroalkylation unit 12. The hydroalkylation unit 12 contains a bed of a bifunctional catalyst which comprises a hydrogenation component and a solid acid alkylation component and which converts at least part of the toluene to (methylcyclohexyl)toluene (MCHT). The effluent from the hydroalkylation unit 12, comprising MCHT and unreacted toluene is then fed via line 13 to a dehydrogenation unit 14 where the MCHT is dehydrogenated to produce dimethylbiphenyl (DMBP) and hydrogen.

The effluent from the dehydrogenation unit 14 is then fed via line 15 to a distillation unit 16, where the 3,3', 3,4'- and 4,4'-DMBP isomers are separated and removed via line 17, a heavy fraction removed via line 18 and a light fraction via line 19. More volatile unreacted MCHT and 2,X'-DMBP isomers are separated and removed via line 20. This mixture is feed to hydrogenation/transalkylation unit 21 to convert the 2,X'-DMBP isomers to MHCT isomers. The effluent from the hydrogenation/transalkylation unit 21 is fed via line 30 to the dehydrogenation unit 14 to produce DMBP isomers.

The raw DMBP-containing product leaving the distillation unit is then fed via line 17 to crystallization unit 22 which preferentially crystallizes 4,4'-DMBP which exits the crystallization unit as product via line 23. The remaining 4,4'-DMBP deficient stream which is concentrated in 3,3'- and 3,4'-DMBP exits via line 24. The mixture of 3,3'- and 3,4'-DMBP is then fed via line 24 to adsorption unit 25 which separates the 3,4'-DMBP via line 26 from 3,3'-DMBP via line 27.

Optionally, some or all of stream 24 may be fed via line 28 to isomerization unit 32, which affords a mixture of DMBP isomers. This affords flexibility to the process whereby the relative amounts of each of the DMBP isomers may be controlled based on market needs. The effluent from the isomerization unit is fed via line 33 to the distillation column. Optionally, and depending on stream content, the output of the isomerization unit may be wholly or partly fed to the crystallization unit via line 34. Optionally, purge line 31 removes 1,X'-MHCTs and CPTs.

Preparation of Metal Cation Treated Zeolite Adsorbents

The following general method was followed. About 100 g of NaY zeolite (Grace-Davison) was mixed with about 1000 g of a 0.4 M solution of the metal chloride in water. The mixture was left for 1 hr at ambient temperature, filtered and the filter cake washed with 3 L of water. The procedure was repeated using a 0.2 M metal chloride solution in water and the filter cake dried at 100° C. and then calcined in air for 2 hours at 300° C. The process was repeated twice more using 0.2 M metal chloride solution and the final filter cake dried at 110° C. Elemental compositions of some of the adsorbents prepared are shown in Table 5. USY 390 is a comparative example. The remaining zeolites are examples according to the present disclosure.

TABLE 5

Elemental composition of zeolites used in adsorption experiments

| Mole ratio | USY 390 | NaY | MgY | KY | SrY | CsY | KBeta |
|---|---|---|---|---|---|---|---|
| Si/Al | 315 | 2.42 | 2.55 | 2.44 | 2.55 | 2.56 | 5.16 |
| Na/Al | 0.23 | 0.98 | 0.19 | 0.07 | 0.11 | 0.26 | 0 |
| Mg/Al | 0 | 0 | 0.39 | 0 | 0 | 0 | 0 |
| K/Al | 0 | 0 | 0 | 0.94 | 0 | 0 | 0.93 |
| Sr/Al | 0 | 0 | 0 | 0 | 0.47 | 0 | 0 |
| Cs/Al | 0 | 0 | 0 | 0 | 0 | 0.65 | 0 |

Preparation of Nano-Crystallite Zeolites

To a plastic beaker while stirring vigorously was added 146.64 g of distilled water to 57.96 g of tetrapropylammonium hydroxide (TPA-OH). Stirring was continued and 98.95 g of tetraethylorthosilicate (TEOS) was added to the mixture. This was allowed to stir covered (foil over top of beaker) for 4 hours. After 4 hours, the beaker was uncovered and the mixture allowed to stir for ~16 h. The mixture was then poured into 300 cc autoclave and heated to 90° C. at a rate of 0.5 C/min and held at a temperature of 90° C. for 70 h. The product was discharged from the autoclave and centrifuged. It was washed three times with water and centrifuged each time. The white crystalline product was dried in a drying oven at 100° C. overnight and then calcined in a calcination furnace by ramping to 600° C. at 5° C./min in air and holding at 600° C. overnight ~16 h. The product had a crystallite size of <100 nm as determined by scanning electron microscopy.

Batch Adsorption Experiments

Various adsorbents were evaluated for the separation of dimethyl biphenyl (DMBP) isomer mixtures utilizing batch experiments. The adsorbents were dried under vacuum at 220° C. The dried solid materials were placed in a vial along with DMBP mixture solution. The DMBP mixture solution was prepared by diluting a mixture of the isomers comprising about 25% by weight 3,3'-isomer, 55% by weight 3,4'-isomer and 20% by weight 4,4'-isomer in a solvent such as isooctane or mesitylene. The total DMBP isomer content in the starting liquid phase was about 10% by weight. All the preparations were performed in an inert atmosphere dry box to minimize moisture exposure. The liquid/solid mixture was then agitated in a shaker at room temperature overnight (>16 hrs). The supernatant liquid phase was subsequently analyzed by gas chromatography (GC) to obtain the DMBP concentration. Solvents used were ACS grade or higher as available. DMBP isomer mixtures were either synthesized in house via methods described in, for example, WO 2015/112252, or prepared using purchased pure isomers.

Isolation of 3,4'-DMBP

Figure 12:
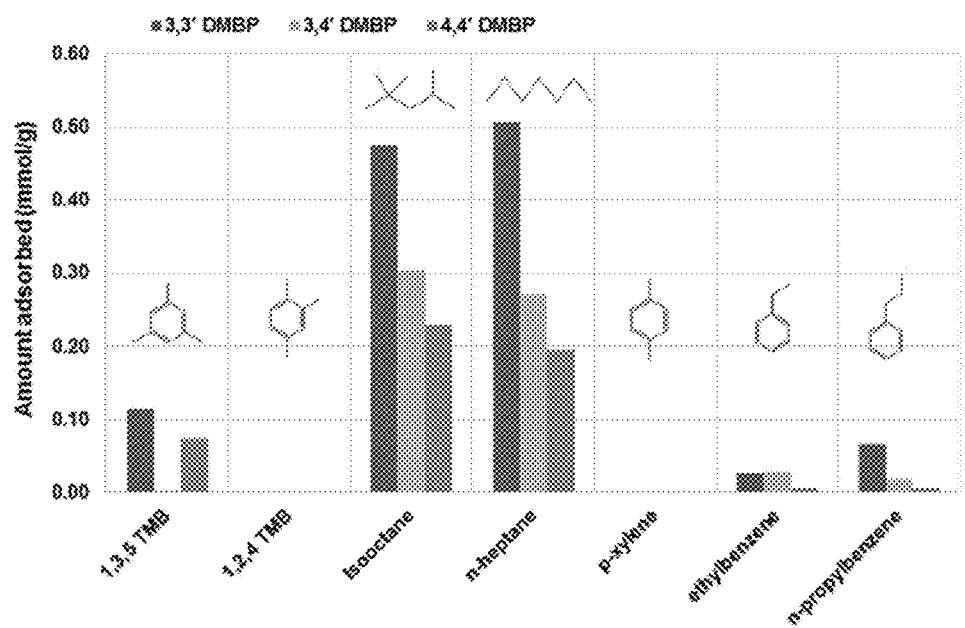
FIG. 12 is bar chart illustrating the effect of different solvents on the adsorption of 3,3'-DMBP, 3,4'-DMBP and 4,4'-DMBP on zeolite Y comprising potassium cations.

FIG. 12 illustrates the results of batch adsorption experiments with various solvents and utilizing Y zeolite treated with potassium cations. The solvents examined were 1,3,5-trimethylbenzene (1,3,5-TMB), 1,2,4-trimethylbenzene (1,2,4-TMB), iso-octane, n-heptane, p-xylene, ethylbenzene and n-propylbenzene. For each solvent the amount of each DMBP isomer adsorbed is indicated in mmol/g. The larger the bar the more of a particular isomer is adsorbed. For each solvent the bars represent 3,3'-DMBP, 3,4'-DMBP and 4,4'-DMBP from left to right respectively. It is apparent that the solvent choice causes different adsorption selectivity for different DMBP isomers. In the cases of 1,2,4-TMB and p-xylene no adsorption of any of the isomers was observed. Use of mesitylene (1,3,5-trimethylbenzene) shows selective adsorption of 3,3'- and 4,4'-DMBP. This selectivity allows isolation of 3,4'-DMBP from the mixture. Use of paraffinic solvents, like isooctane and n-heptane, results in a greater adsorption of 3,3'-DMBP.

Isolation of 4,4'-DMBP

Figure 13:
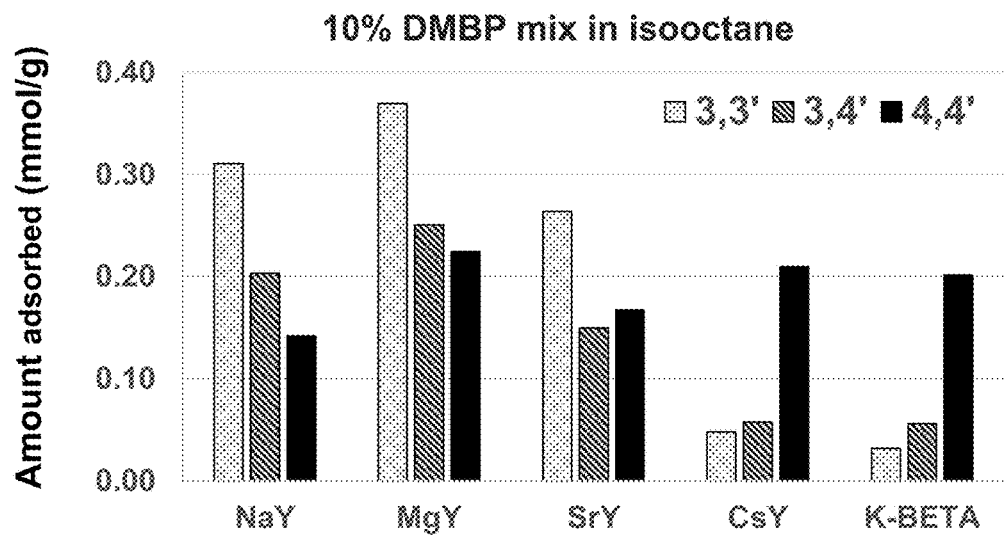
FIG. 13 is a bar chart illustrating the relative adsorptions of 3,3'-DMBP, 3,4'-DMBP and 4,4'-DMBP with various metal cation containing Y zeolites and potassium cation containing Beta zeolite using isooctane as a solvent.

FIG. 13 illustrates the results of batch adsorption experiments with isooctane as a solvent and magnesium, strontium and cesium treated Y zeolite. The cesium treated Y zeolite (CsY) adsorbs the 4,4' isomer more selectively than the other two isomers. This is surprising because other cation treated Y zeolites such as magnesium Y (MgY) and strontium Y (SrY) adsorb the 3,3' isomer more preferentially as found for KY. Adsorption of the 4,4'-isomer on CsY was three to four times higher than that of the other two isomers. Further, Beta zeolite treated with potassium cations indicated strong adsorption of the 4,4'-isomer.

Figure 14:
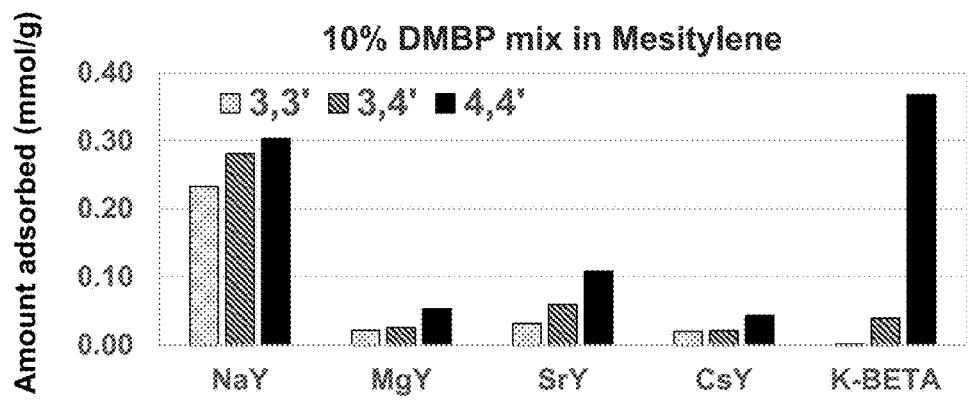
FIG. 14 is a bar chart illustrating the relative adsorptions of 3,3'-DMBP, 3,4'-DMBP and 4,4'-DMBP with various metal cation containing Y zeolites and potassium cation containing Beta zeolite using mesitylene as a solvent.

FIG. 14 illustrates the results of batch adsorption experiments with mesitylene as a solvent and magnesium, strontium and cesium treated Y zeolite and potassium treated Beta zeolite. Use of mesitylene causes selective adsorption of the 4,4'-isomer on all of these zeolites. Adsorption of the 4,4' isomer on the adsorbents was twice or more as compared to that of the other two isomers. All adsorptions of DMBP with mesitylene solvent were lower than those obtained with isooctane solvent, however K-Beta zeolite showed high and very selective adsorption of the 4,4'-isomer.

Isolation of 4,4'-DMBP

Figure 15:
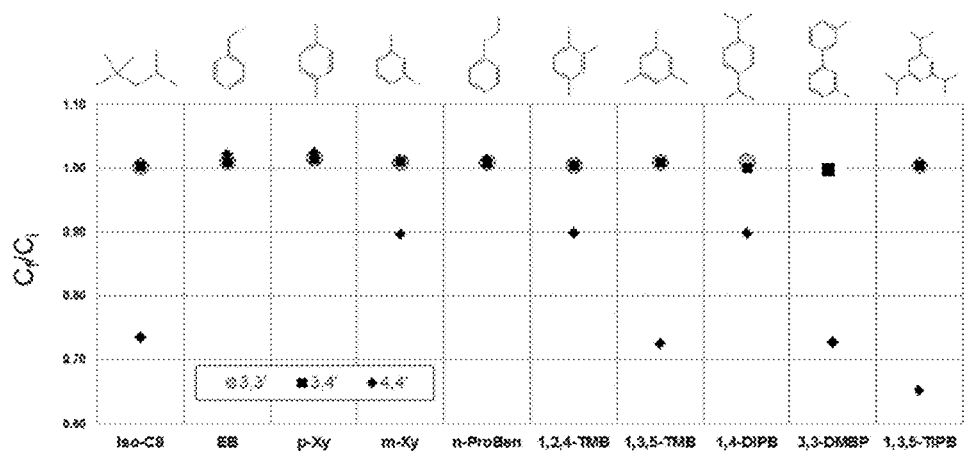
FIG. 15 is a plot of concentration changes (Cf/Ci) in the liquid phase after adsorption of DMBP isomers on ZSM-5 zeolite using various solvents at room temperature.

FIG. 15 illustrates the results of batch adsorption experiments with various solvents and utilizing ZSM-5 zeolite having a crystallite size between 2 and 5 μm and a Si/Al ratio of 220. The sodium content was <0.03 wt. %. The solvents examined were iso-octane, ethylbenzene, p-xylene, m-xylene, n-propylbenzene, 1,2,4-trimethylbenzene (1,2,4-TMB), 1,3,5-trimethylbenzene (1,3,5-TMB), 1,4-diisopropylbenzene, 3,3-DMBP and 1,3,5-triisopropylbenzene. For each solvent the amount of each DMBP isomer adsorbed is shown. The smaller the value of $C_f/C_i$, the more of a particular isomer is adsorbed. Ci is the initial concentration in the liquid phase and Cf is the final concentration in the liquid phase. It is apparent that ZSM-5 selectively adsorbs 4,4'-DMBP from a mixture of the isomers and that the solvent choice causes different adsorption selectivity for 4,4'-DMBP. Significantly, none of the solvents showed any adsorption of the other two isomers. This indicates 3,3'- and 3,4'-DMBP are excluded from the pores, allowing isolation of 4,4'-DMBP from the mixture. It also illustrates the strong effect of the solvents on how much of 4,4'-DMBP is adsorbed. Different solvents cause different degrees of adsorption. Bulkier solvent molecules, such as isooctane (2,2,4 trimethylpentane), mesitylene (1,3,5-trimethylbenzene), 1,4-diisopropylbenzene, and 1,3,5-triisopropylbenzene, result in more penetration of 4,4'-DMBP into the pores. Aromatic solvents with more branched alkyl chains (e.g. mesitylene and 1,2,4-trimethylbenzene) result in higher loading than those substituted with linear alkyl chains (e.g. n-propylbenzene).

Figure 16:
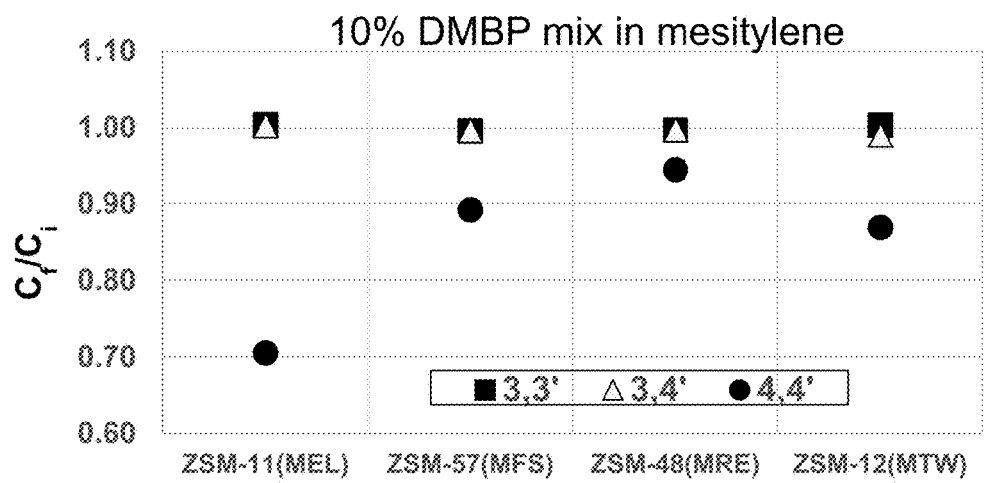
FIG. 16 is a plot of concentration changes (Cf/Ci) in the liquid phase after adsorption of DMBP isomers on various ZSM zeolite frameworks in mesitylene solvent at room temperature.

FIG. 16 is a plot of concentration changes (Cf/Ci) in the liquid phase after adsorption of DMBP isomers on various ZSM zeolite frameworks in mesitylene solvent at room temperature. In each case it can be seen that selective adsorption of the 4,4'-isomer occurred.

Influence of Crystallite Size

Figure 17:
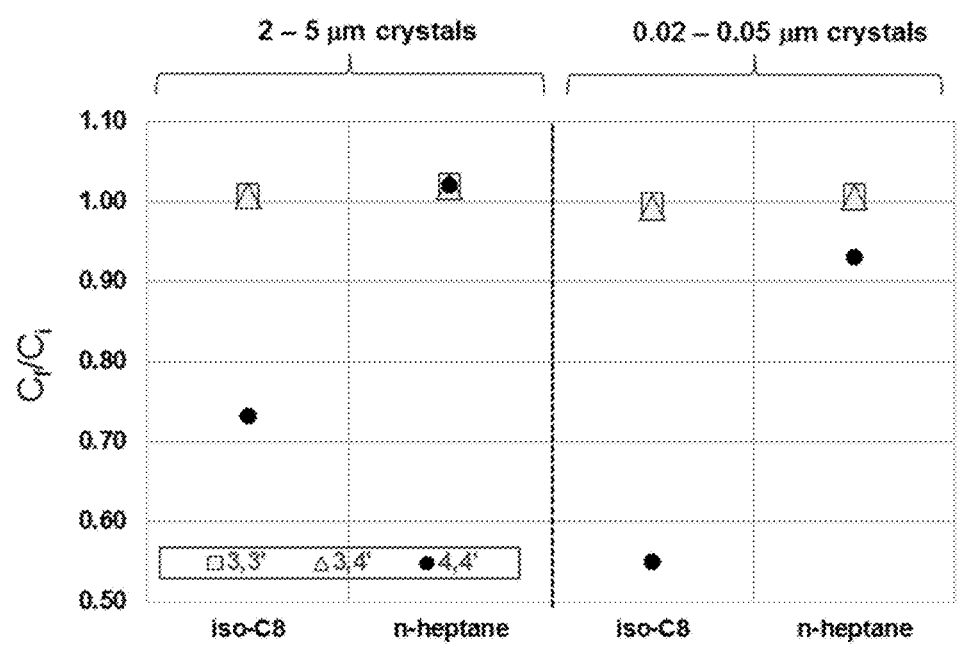
FIG. 17 is a plot of concentration changes (Cf/Ci) in the liquid phase after adsorption of DMBP isomers on two different sizes of ZSM-5 zeolite at room temperature.

FIG. 17 compares the effect of the size of the zeolite crystallites on 4,4'-DMBP adsorption. The batch experimental data indicates that the small crystallite ZSM-5 (MFI) zeolite gives higher 4,4'-DMBP loading than the larger crystallite zeolite. For example, with n-heptane as the solvent, there was no selective adsorption of 4,4'-DMBP observed with the large crystallite zeolite, whereas the small crystallite zeolite gave selective adsorption.

Continuous Breakthrough Experiments

A liquid chromatographic system was used for the breakthrough study of the adsorbents at elevated temperature. Adsorbents were packed into 4.6 mm ID×100 mm long stainless steel columns with 0.5 micron frits at each end. The adsorbents were dried at 300° C. for 1 hour in a flow of dry nitrogen. A packed column was equilibrated at 150° C. or 177° C. with a solvent (i.e. the mobile phase) prior to injection. The DMBP mixture solution (10 wt. % or 25 wt. %) was prepared in the same solvent as the mobile phase and introduced to a column through injection of a 6.6 ml pulse. The flow rate of solvent was set at 0.4 ml/min. Effluent from the column was collected in a fraction collector and the concentrations of DMBP in the fractions were determined by GC.

Isolation of 3,3'-DMBP

Figure 18:
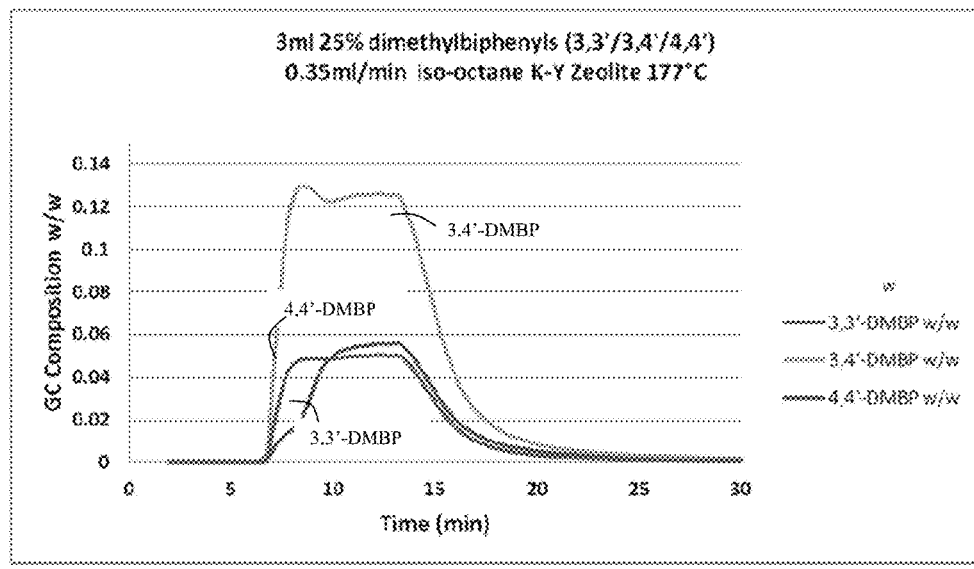
FIG. 18 illustrates the breakthrough curves for a mixture of 3,3'-DMBP, 3,4'-DMBP and 4,4'-DMBP in iso-octane solvent fed into a column containing Y zeolite containing potassium cations at 177° C.

A 3 ml pulse of 25 wt. % DMBP isomer mixture in iso-octane was introduced to a column containing potassium zeolite (Y-zeolite). FIG. 18 illustrates the breakthrough curves. The 3,3'-isomer was clearly retained as compared to the 4,4'-isomer and the 3,4'-isomer.

Figure 19:
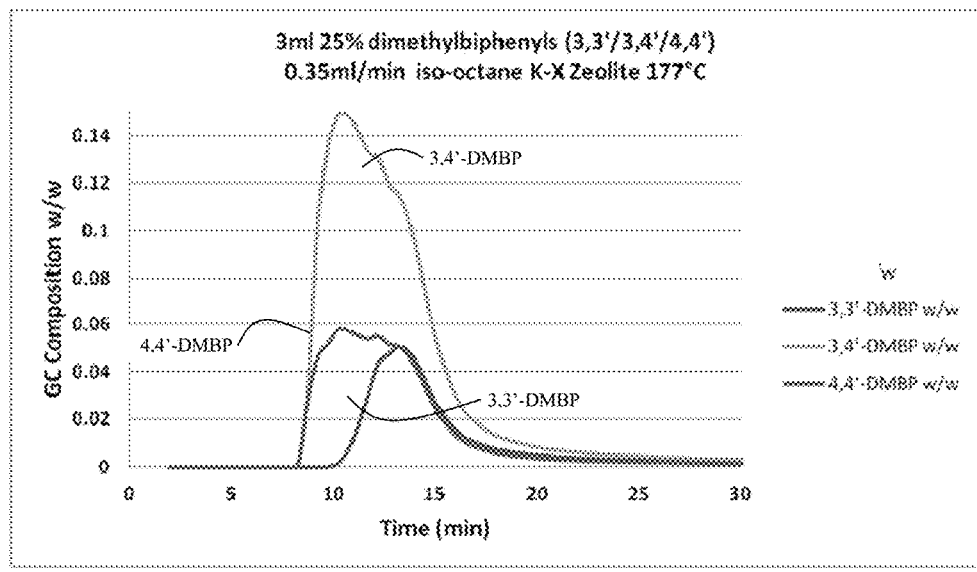
FIG. 19 illustrates the breakthrough curves for a mixture of 3,3'-DMBP, 3,4'-DMBP and 4,4'-DMBP in iso-octane solvent fed into a column containing X zeolite containing potassium cations at 177° C.

A 3 ml pulse of 25 wt. % DMBP isomer mixture in iso-octane was introduced to a column containing potassium zeolite (X-zeolite). FIG. 19 illustrates the breakthrough curves. The 3,3'-isomer was clearly retained as compared to the 4,4'-isomer and the 3,4'-isomer.

Figure 20:
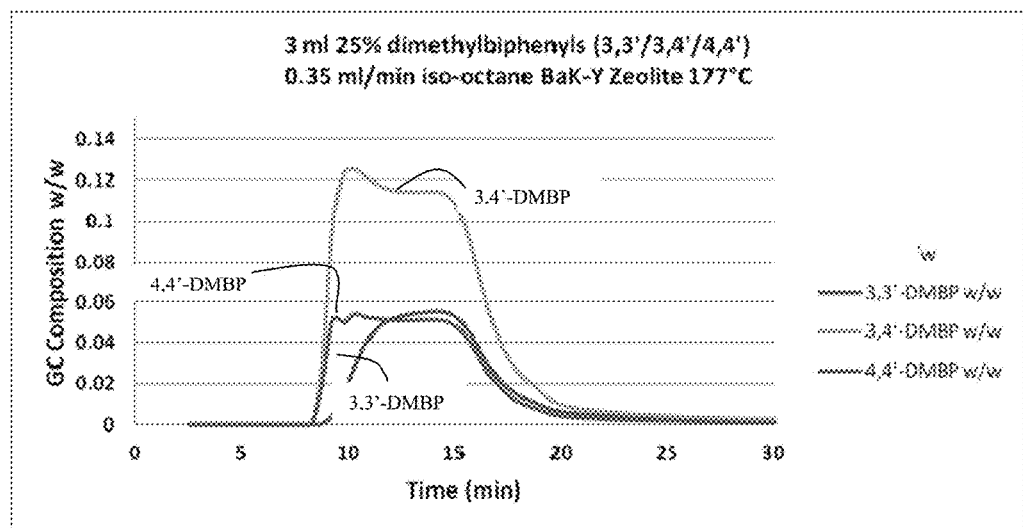
FIG. 20 illustrates the breakthrough curves for a mixture of 3,3'-DMBP, 3,4'-DMBP and 4,4'-DMBP in iso-octane solvent fed into a column containing Y zeolite containing potassium and barium cations at 177° C.

A 3 ml pulse of 25 wt. % DMBP isomer mixture in iso-octane was introduced to a column containing potassium barium zeolite (Y-zeolite). FIG. 20 illustrates the breakthrough curves. The 3,3'-isomer was clearly retained as compared to the 4,4'-isomer and the 3,4'-isomer.

Figure 21:
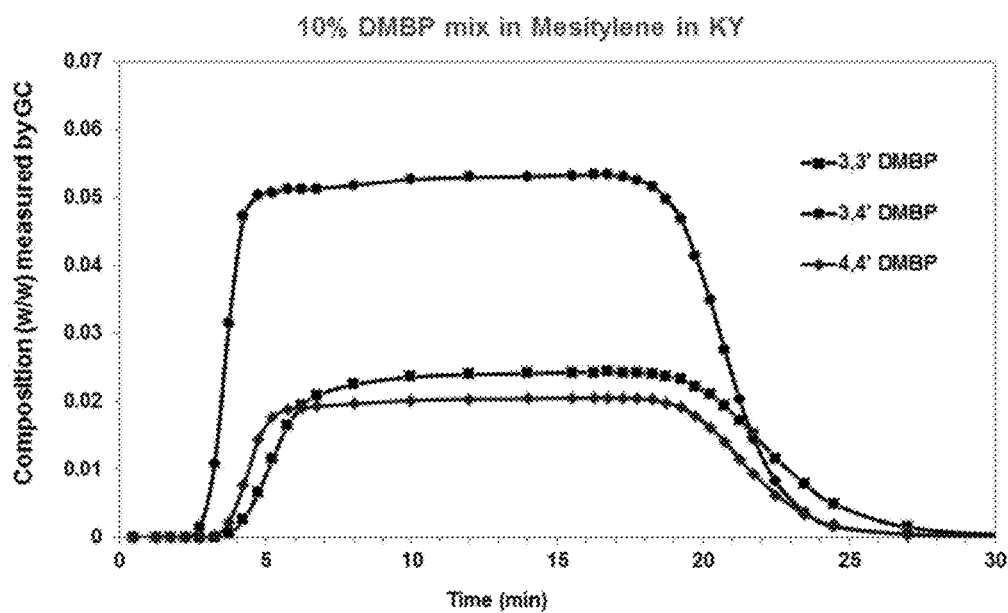
FIG. 21 illustrates the breakthrough curves for a mixture of 3,3'-DMBP, 3,4'-DMBP and 4,4'-DMBP in mesitylene solvent fed into a column containing Y zeolite containing potassium cations at 150° C.

Separation of the DMBP mixture on the KY with mesitylene was further tested in a liquid chromatographic system to validate the batch experiment data at the elevated temperature (150° C.). As shown in FIG. 21, the breakthrough point of the 3,4'-isomer is earlier than the other two isomers. This indicates no adsorption of the 3,4'-isomer, while the other two isomers show delayed breakthrough points due to their retention. The selective adsorption of the two isomers is consistent with what was observed from the batch experiment. The non-adsorbed isomer may be removed from the adsorbent and the adsorbed two isomers then recovered by desorption. The data also shows the 3,3' isomer is preferred to the 4,4'-isomer, thus presenting the possibility of separation of these two isomers into individual components.

Figure 22:
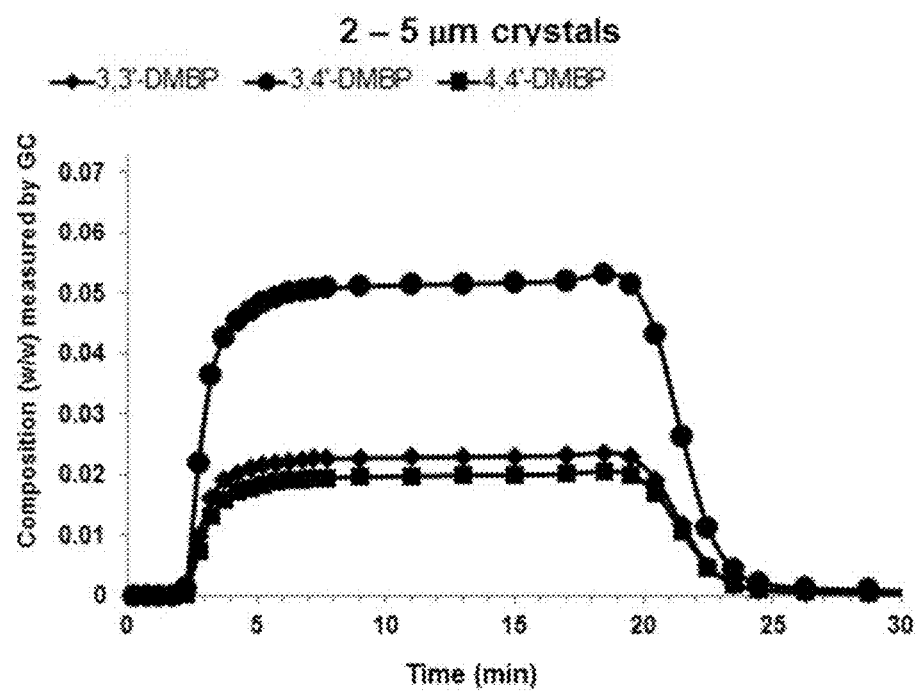
FIG. 22 illustrates the breakthrough curves for a mixture of 3,3'-DMBP, 3,4'-DMBP and 4,4'-DMBP in n-heptane solvent fed into a column containing ZSM-5 zeolite (2-5 µm crystallite size) at 150° C.
Figure 23:
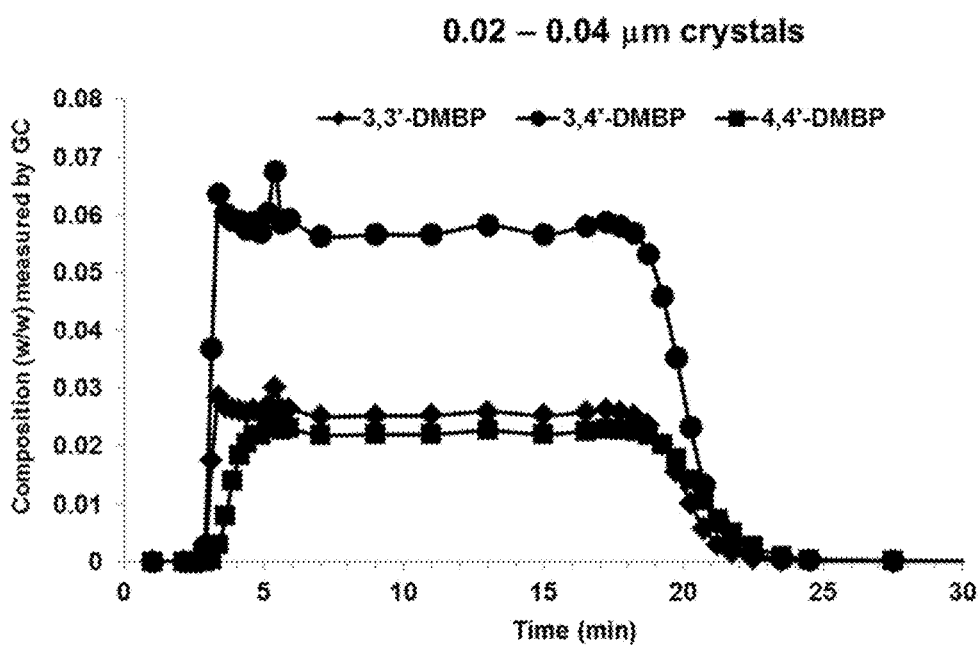
FIG. 23 illustrates the breakthrough curves for a mixture of 3,3'-DMBP, 3,4'-DMBP and 4,4'-DMBP in n-heptane solvent fed into a column containing ZSM-5 zeolite (0.02-0.04 µm crystallite size) at 150° C.

The effect of crystallite size was further tested by the breakthrough studies illustrated in FIGS. 22 and 23. A 3 ml pulse of 10 wt. % DMBP isomer mixture in n-heptane was introduced into columns containing large (2-5 micron) or small (<100 nm) crystallite sizes. The same trend that the small crystallite size increases adsorption of the 4,4'-isomer was observed. With n-heptane as the mobile phase, all three isomers eluted at the same time from the large crystallite zeolite column (FIG. 22), and their breakthrough times indicates no retention of these isomers. However, the small crystallite ZSM-5 (MFI) zeolite (FIG. 23) resulted in adsorption of 4,4'-DMBP under the same conditions, as evidenced by the delayed breakthrough point.

Figure 24:
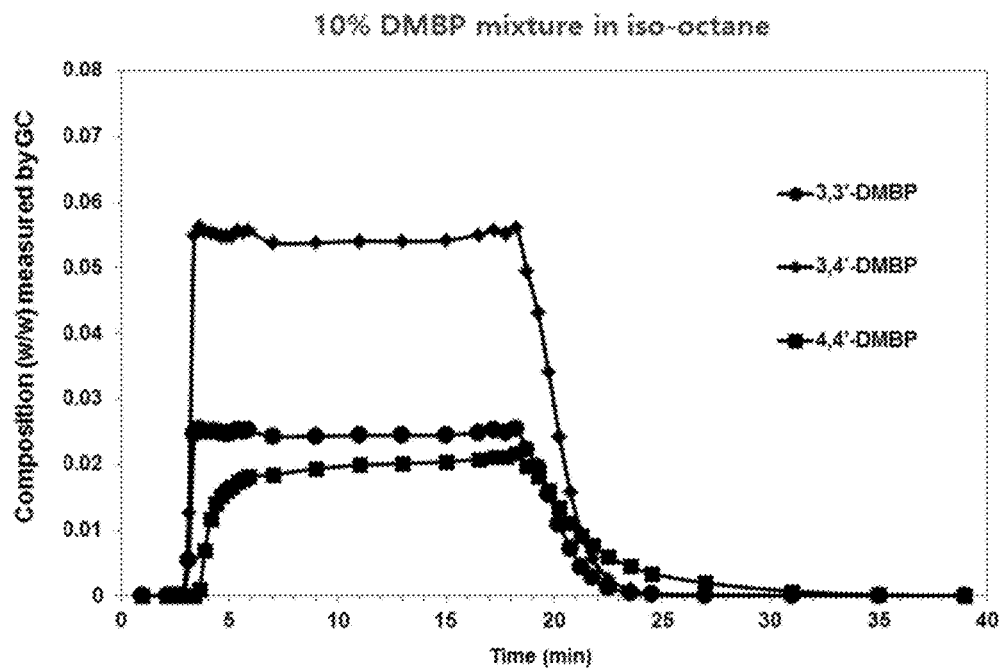
FIG. 24 illustrates the breakthrough curves for a mixture of 3,3'-DMBP, 3,4'-DMBP and 4,4'-DMBP in iso-octane solvent fed into a column containing ZSM-5 zeolite (0.02-0.04 µm crystallite size) at 150° C.
Figure 25:
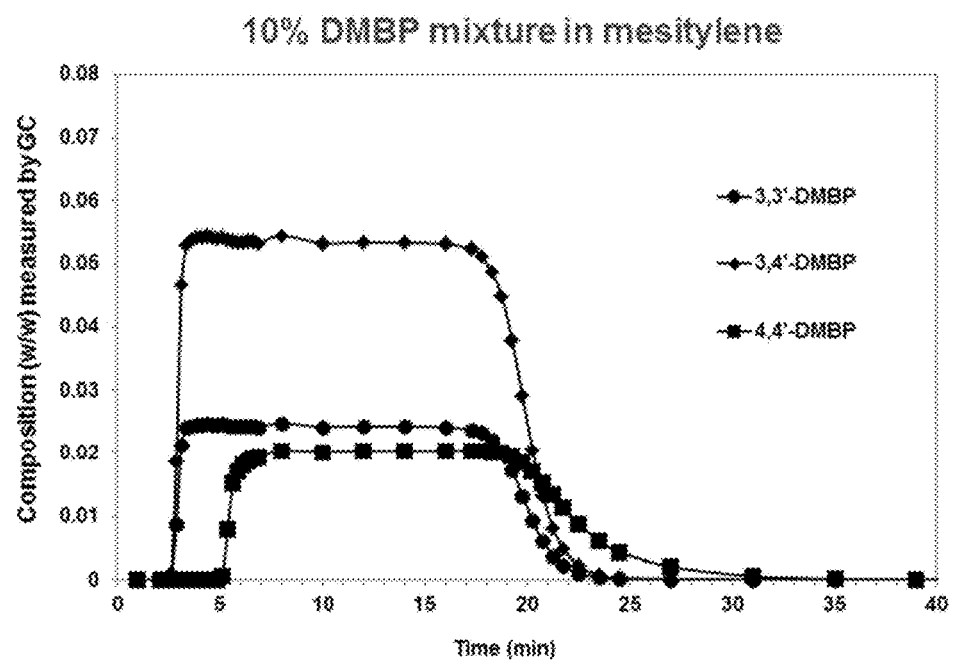
FIG. 25 illustrates the breakthrough curves for a mixture of 3,3'-DMBP, 3,4'-DMBP and 4,4'-DMBP in mesitylene solvent fed into a column containing ZSM-5 zeolite (0.02-0.04 µm crystallite size) at 150° C.

The effect of the solvent was also demonstrated by a breakthrough study at elevated temperature (150° C.). FIGS. 24 and 25 compare the breakthrough curves with different solvent systems and their impact on 4,4'-DMBP adsorption. Iso-octane and n-heptane are both paraffinic, but the branched bulkier iso-octane (FIG. 24) results in 4,4'-DMBP adsorption which is about two times higher than with n-heptane. The even bulkier mesitylene solvent (FIG. 25) increases the adsorption even more as compared to that with iso-octane. About three times more of 4,4'-DMBP adsorption was observed. Regardless of solvents tested, the 3,3' and 3,4'-DMBP isomers were not adsorbed. The ratio of the total peak area under the curves is consistent with the initial composition of the feed, indicating the complete recovery of the DMBP isomers from the column. In the process, the non-adsorbed 3,3'- and 3,4'-DMBP can be removed from adsorbents and the adsorbed 4,4'-DMBP is then recovered by desorption.

Comparative Example

Figure 26:
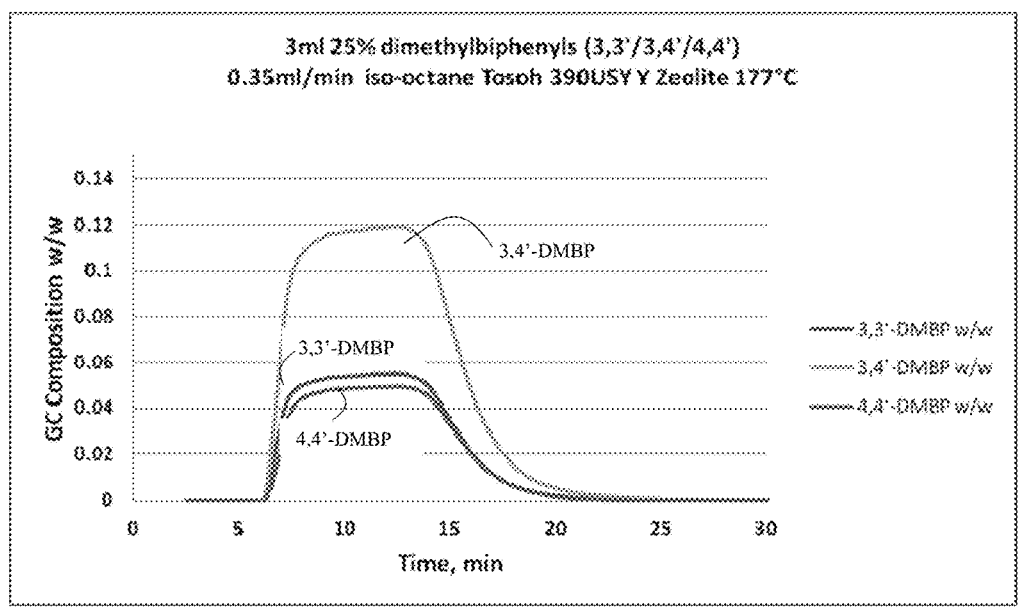
FIG. 26 illustrates the breakthrough curves for a mixture of 3,3'-DMBP, 3,4'-DMBP and 4,4'-DMBP in iso-octane solvent fed into a column containing high silica USY at 177° C.

For comparison, and to illustrate the effect of the metal cations in the zeolite, a high silica low metal cation faujasite (390 USY) was packed into a column and tested. This material has a high Si/Al ratio of 315 and a low Na/Al ratio of 0.23. FIG. 26 illustrates no selectivity for any of the isomers over the others.

Further illustrative, non-exclusive examples of methods according to the present disclosure are presented in the following enumerated paragraphs.

1. A process for producing one or more 3,3'-, 3,4'- and 4,4'-dimethyl biphenyl isomers, the process comprising:
(a) contacting a feed comprising toluene with hydrogen in the presence of a hydroalkylation catalyst under conditions effective to produce a hydroalkylation reaction product comprising (methylcyclohexyl)toluenes;
(b) dehydrogenating at least part of the hydroalkylation reaction product in the presence of a dehydrogenation catalyst under conditions effective to produce a dehydrogenation reaction product comprising said dimethyl biphenyl isomers;
(c) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and (d) separating the 3,3'-, 3,4'- and 4,4'-dimethyl biphenyl isomers, wherein said separation comprises at least one selective adsorption.

2. A process for producing one or more 3,3'-, 3,4'- and 4,4'-dimethyl biphenyl isomers, the process comprising:
(a) contacting a feed comprising benzene with hydrogen in the presence of a hydroalkylation catalyst under conditions effective to produce a hydroalkylation reaction product comprising cyclohexylbenzenes;
(b) dehydrogenating at least part of the hydroalkylation reaction product in the presence of a dehydrogenation catalyst under conditions effective to produce a dehydrogenation reaction product comprising biphenyl;
(c) reacting at least part of the dehydrogenation reaction product with a methylating agent in the presence of an alkylation catalyst under conditions effective to produce a methylation reaction product comprising said dimethyl biphenyl isomers;
(d) separating the methylation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and
(e) separating the 3,3'-, 3,4'- and 4,4'-dimethyl biphenyl isomers, wherein said separation comprises at least one selective adsorption.

3. A process for producing one or more 3,3'-, 3,4'- and 4,4'-dimethyl biphenyl isomers, the process comprising;
(a) oxidizing a feed comprising benzene in the presence of an oxidative coupling catalyst under conditions effective to produce an oxidation reaction product comprising biphenyl;
(b) reacting at least part of the oxidation reaction product with methylating agent in the presence of an alkylation catalyst under conditions effective to produce a methylation reaction product comprising said dimethyl biphenyl isomers;
(c) separating the methylation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and
(d) separating the 3,3'-, 3,4'- and 4,4'-dimethyl biphenyl isomers, wherein said separation comprises at least one selective adsorption.

4. A process for producing one or more 3,3'-, 3,4'- and 4,4'-dimethyl biphenyl isomers, the process comprising:
(a) thermally treating a feed comprising benzene under conditions effective to produce a dehydrocondensation product comprising biphenyl;
(b) reacting at least part of the dehydrocondensation product with methylating agent in the presence of an alkylation catalyst under conditions effective to produce a methylation reaction product comprising said dimethyl biphenyl isomers;
(c) separating the methylation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and
(d) separating the 3,3'-, 3,4'- and 4,4'-dimethyl biphenyl isomers, wherein said separation comprises at least one selective adsorption.

5. A process according to any one of paragraphs 1 to 4, wherein the separation into at least a first stream and at least one second stream comprises distillation and/or crystallization.

6. A process according to any one of paragraphs 1 to 5, wherein the separation of the 3,3'-, 3,4'- and 4,4'-dimethyl biphenyl isomers in the first stream comprises:
(i) contacting the first stream with a first adsorbent thereby selectively adsorbing at least one of the 3,3'-, 3,4'- and 4,4'-dimethyl biphenyl isomers within the adsorbent;
(ii) withdrawing from said first adsorbent a raffinate stream comprising less selectively adsorbed dimethyl biphenyl isomers; and
(iii) withdrawing from said first adsorbent a first extract stream comprising said selectively adsorbed dimethyl biphenyl isomers.

7. A process according to paragraph 6, further comprising:
(i) contacting the raffinate stream with a second adsorbent thereby selectively adsorbing one of the dimethyl biphenyl isomers less selectively adsorbed by the first adsorbent; and
(ii) withdrawing from said second adsorbent a second extract stream comprising a less selectively adsorbed dimethyl biphenyl isomer and a third extract stream comprising said selectively adsorbed dimethyl biphenyl isomer.

8. A process according to paragraph 6, further comprising selectively crystallizing one of the 3,3'-, 3,4'- and 4,4'-dimethyl biphenyl isomers from the raffinate stream.

9. A process according to any one of paragraph 1 to 5, wherein the separation of the 3,3'-, 3,4'- and 4,4'-dimethyl biphenyl isomers in the first stream comprises:
(i) separating by crystallization at least one of the isomers to provide a solid product and a raffinate stream comprising non-crystallizing isomers;
(ii) contacting the raffinate stream with an adsorbent thereby selectively adsorbing at least one of the non-crystallizing isomers within the adsorbent;
(iii) withdrawing from said adsorbent an extract stream comprising the less selectively adsorbed dimethyl biphenyl isomer or isomers; and
(iv) withdrawing from said adsorbent another extract stream comprising said selectively adsorbed dimethyl biphenyl isomer or isomers.

10. A process according to any one of paragraphs 1 to 9, further comprising contacting the second stream comprising one or more 2,X'-dimethyl biphenyl isomers (where X=2, 3 or 4) with a hydrogenation catalyst under conditions effective to produce one or more methylcyclohexyl toluene isomers; contacting the said methylcyclohexyl toluene isomers with a transalkylation catalyst under conditions effective to modify the methylcyclohexyl toluene isomer distribution; and contacting the said modified methylcyclohexyl toluene isomer distribution with a dehydrogenation catalyst so as to provide one or more 3,3'-, 3,4'- and/or 4,4'-dimethyl biphenyl isomers.

11. A process according to any one of paragraphs 6 to 10, further comprising contacting any one or more of the raffinate streams with a hydrogenation catalyst under conditions effective to produce one or more methylcyclohexyl toluene isomers, contacting the said methylcyclohexyl toluene isomers with a transalkylation catalyst under conditions effective to modify the methylcyclohexyl toluene isomer distribution and contacting the said modified methylcyclohexyl toluene isomer distribution with a dehydrogenation catalyst so as to provide one or more 3,3'-, 3,4'- and/or 4,4'-dimethyl biphenyl isomers.

12. A process according to any one of paragraphs 6 to 11, further comprising contacting one or more of the extract streams from the first and/or second adsorbent with a hydrogenation catalyst under conditions effective to produce one or more methylcyclohexyl toluene isomers, contacting the said methylcyclohexyl toluene isomers with a transalkylation catalyst under conditions effective to modify the methylcyclohexyl toluene isomer distribution and contacting the said modified methylcyclohexyl toluene isomer distribution with a dehydrogenation catalyst so as to provide one or more 3,3'-, 3,4'- and/or 4,4'-dimethyl biphenyl isomers.

13. A process according to any one of paragraphs 10 to 12, further comprising feeding at least part of the contact products produced by the hydrogenation/transalkylation catalysts to the separation step of any one of claims 1 to 4 which affords at least a first stream and at least one second stream.

14. A process according to any one of paragraphs 10 to 13, further comprising feeding at least part of the contact products produced by the hydrogenation/transalkylation catalysts to the dehydrogenation step (b) of claim 1.

15. A process according to any one of paragraphs 10 to 14, wherein the hydrogenation catalyst and the transalkylation catalyst are either the same catalysts or different catalysts.

16. A process according to any one of paragraphs 10 to 15, wherein the hydrogenation catalyst and the transalkylation catalyst are located in the same reactor or in different reactors.

17. A process according to any one of paragraphs 6 to 16, further comprising contacting at least part of any one or more of the raffinate streams with an isomerization catalyst under conditions effective to produce a mixture of isomers comprising the previously extracted dimethyl biphenyl isomer(s).

18. A process according to any one of paragraphs 6 to 17 further comprising contacting at least part of one or more of the extract streams with an isomerization catalyst under conditions effective to produce a mixture of isomers comprising the previously extracted dimethyl biphenyl isomer(s).

19. A process according to any one of paragraphs 17 or 18, wherein at least part of the mixture of isomers is fed to the separation step of any one of paragraphs 1 to 4 which affords at least a first stream and at least one second stream.

20. A process according to any one of paragraphs 17 to 19, wherein at least part of the mixture is fed to the first adsorption unit and/or subjected to crystallization to separate at least one of the isomers as a solid product.

21. A process according to any one of paragraphs 1 to 20, wherein the selective adsorption is performed in the presence of one or more solvents.

22. A process according to paragraph 21, wherein the solvent comprises an aromatic hydrocarbon, a saturated hydrocarbon or combinations thereof.

23. A process according to any one of paragraphs 1 to 22, wherein the first stream comprising the 2,X'-DMBP isomers, where X=2, 3 or 4, further comprises one or more of cyclopentadienyl toluenes (CPDTs), 4-methylcyclohexyl toluenes (4,X'-MCHTs), 3-methylcyclohexyl toluenes (3,X'-MCHTs), 2-methylcyclohexyl toluenes (2,X'-MCHT), ethyl- or dimethyl-cyclopentyl toluenes (CPTs), 1-methylcyclohexyl toluenes (1,X'-MCHTs) and dimethyl bicyclohexanes (DMBCHs).

24. A process according to any one of paragraphs 1 to 23, wherein the feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) comprises 5-50% by weight 3,3'-isomer, 5-80% by weight 3,4'-isomer and 5-90% by weight 4,4'-isomer based on the total weight of the three isomers.

25. A process according to any one of paragraphs 1 to 24, wherein the feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) comprises 10-40% by weight 3,3'-isomer, 20-70% by weight 3,4'-isomer and 5-30% by weight 4,4'-isomer based on the total weight of the three isomers.

26. A process according to any one of paragraphs 1 to 25, wherein the feed which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) comprises 15-35% by weight 3,3'-isomer, 40-70% by weight 3,4'-isomer and 5-30% by weight 4,4'-isomer based on the total weight of the three isomers.

27. A process according to any one of paragraphs 17 to 26, wherein the isomerization catalyst contact product comprises 10-60% by weight 3,3'-isomer, 10-60% by weight 3,4'-isomer, 2-30% by weight 4,4'-isomer and 2-30% by weight 2,X'-isomers (where X=2, 3 or 4) based on the total weight of the isomers.

28. A process according to any one of paragraphs 17 to 27, wherein the isomerization catalyst contact product comprises 20-55% by weight 3,3'-isomer, 20-55% by weight 3,4'-isomer, 5-20% by weight 4,4'-isomer and 5-25% by weight 2,X'-isomers (where X=2, 3 or 4) based on the total weight of the isomers.

29. A process according to any one of paragraphs 17 to 28, wherein the isomerization catalyst contact product comprises about 37% by weight 3,3'-isomer, about 38% by weight 3,4'-isomer, about 10% by weight 4,4'-isomer and about 13% by weight 2,X'-isomers (where X=2, 3 or 4) based on the total weight of the isomers.

30. A process for separating one or more dimethyl biphenyl isomers 3,3'-, 3,4'- and 4,4'-DMBP from a feed comprising two or more of said isomers, wherein the separation comprises one or more selective adsorptions.

31. A process according to paragraph 30, wherein the separation comprises two selective adsorptions.

32. A process according to paragraph 31, wherein the two selective adsorptions comprise different adsorbents.

33. A process according to paragraph 30, wherein the feed is derived from a separation of a stream comprising one or more dimethyl biphenyl isomers 3,3'-, 3,4'- and 4,4'-DMBP, and one or more 2,X'-dimethyl biphenyl isomers (where X=2, 3 or 4).

34. A process according to any one of paragraphs 1 to 33, wherein the at least one selective adsorption comprises a simulated moving bed, membrane separation or semi-batch (swing) adsorption.

35. A process according to any one of paragraphs 1 to 34, wherein the at least one selective adsorption comprises contacting the mixture of dimethyl biphenyl isomers with at least one zeolite, wherein said zeolite has a largest diffuse along dimension of at least about 4 Angstroms (Å).

36. A process according to any one of paragraphs 1 to 35, wherein the at least one selective adsorption comprises contacting the mixture of dimethyl biphenyl isomers with at least one zeolite, wherein said zeolite comprises one or more metal cations in the +1 or +2 oxidation states.

37. A process according to any one of paragraphs 1 to 36, wherein the at least one selective adsorption comprises contacting the mixture of dimethyl biphenyl isomers with at least one zeolite, wherein said zeolite comprises an average crystallite size less than about 5000 nm, or less than about 1000 nm, or less than about 100 nm.

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the above examples are put forth to provide those skilled in the art with a complete disclosure and description of how to make and use the disclosed compositions, and are not intended to limit the scope of the disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited herein are fully incorporated by reference for all jurisdictions in which such incorporation is permitted and to the extent such disclosure is consistent with the description of the present disclosure.

The invention claimed is:

1. A process for producing one or more 3,3'-, 3,4'- and 4,4'-dimethyl biphenyl isomers, the process comprising:
   (a) contacting a feed comprising toluene with hydrogen in the presence of a hydroalkylation catalyst under conditions effective to produce a hydroalkylation reaction product comprising (methylcyclohexyl)toluenes;
   (b) dehydrogenating at least part of the hydroalkylation reaction product in the presence of a dehydrogenation catalyst under conditions effective to produce a dehydrogenation reaction product comprising said dimethyl biphenyl isomers;
   (c) separating the dehydrogenation reaction product into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4); and
   d) separating the 3,3'-, 3,4'- and 4,4'-dimethyl biphenyl isomers in the first stream, wherein said separation comprises at least one selective adsorption using an adsorbent comprising at least one zeolite, wherein the zeolite structure type comprises BEA, FAU, MFI, MEL, MTW, MOR, LTL, EMT, FER, MAZ, MEI, TON, MWW, EUO, MFS, IMF, MRE, ITN, MTT, MSE or IWV, wherein said zeolite has a largest diffuse along dimension of at least about 4 Angstroms (A).

2. A process according to claim 1, wherein the separation into at least a first stream and at least one second stream comprises distillation and/or crystallization.

3. A process according to claim 1, wherein the separation of the 3,3'-, 3,4'- and 4,4'-dimethyl biphenyl isomers in the first stream comprises:
   (i) contacting the first stream with a first adsorbent thereby selectively adsorbing at least one of the 3,3'-, 3,4'- and 4,4'-dimethyl biphenyl isomers within the adsorbent;
   (ii) withdrawing from said first adsorbent a raffinate stream comprising less selectively adsorbed dimethyl biphenyl isomers; and
   (iii) withdrawing from said first adsorbent a first extract stream comprising said selectively adsorbed dimethyl biphenyl isomers.

4. A process according to claim 3, further comprising:
   (i) contacting the raffinate stream with a second adsorbent thereby selectively adsorbing one of the dimethyl biphenyl isomers less selectively adsorbed by the first adsorbent; and
   (ii) withdrawing from said second adsorbent a second extract stream comprising a less selectively adsorbed dimethyl biphenyl isomer and a third extract stream comprising said selectively adsorbed dimethyl biphenyl isomer.

5. A process according to claim 3, further comprising selectively crystallizing one of the 3,3'-, 3,4'- and 4,4'-dimethyl biphenyl isomers from the raffinate stream.

6. A process according to claim 1, wherein the separation of the 3,3'-, 3,4'- and 4,4'-dimethyl biphenyl isomers in the first stream comprises:
   (i) separating by crystallization at least one of the isomers to provide a solid product and a raffinate stream comprising non-crystallizing isomers;
   (ii) contacting the raffinate stream with an adsorbent thereby selectively adsorbing at least one of the non-crystallizing isomers within the adsorbent;
   (iii) withdrawing from said adsorbent an extract stream comprising the less selectively adsorbed dimethyl biphenyl isomer or isomers; and
   (iv) withdrawing from said adsorbent another extract stream comprising said selectively adsorbed dimethyl biphenyl isomer or isomers.

7. A process according to claim 1, further comprising contacting the second stream comprising one or more 2,X'-dimethyl biphenyl isomers (where X=2, 3 or 4) with a hydrogenation catalyst under conditions effective to produce one or more methylcyclohexyl toluene isomers; contacting the said methylcyclohexyl toluene isomers with a transalkylation catalyst under conditions effective to modify the methylcyclohexyl toluene isomer distribution; and contacting the said modified methylcyclohexyl toluene isomer distribution with a dehydrogenation catalyst so as to provide one or more 3,3'-, 3,4'- and/or 4,4'-dimethyl biphenyl isomers.

8. A process according to claim 3, further comprising contacting any one or more of the raffinate streams with a hydrogenation catalyst under conditions effective to produce one or more methylcyclohexyl toluene isomers, contacting the said methylcyclohexyl toluene isomers with a transalkylation catalyst under conditions effective to modify the methylcyclohexyl toluene isomer distribution and contacting the said modified methylcyclohexyl toluene isomer distribution with a dehydrogenation catalyst so as to provide one or more 3,3'-, 3,4'- and/or 4,4'-dimethyl biphenyl isomers.

9. A process according to claim 4, further comprising contacting one or more of the extract streams from the first and/or second adsorbent with a hydrogenation catalyst under conditions effective to produce one or more methylcyclohexyl toluene isomers, contacting the said methylcyclohexyl toluene isomers with a transalkylation catalyst under conditions effective to modify the methylcyclohexyl toluene isomer distribution and contacting the said modified methylcyclohexyl toluene isomer distribution with a dehydrogenation catalyst so as to provide one or more 3,3'-, 3,4'- and/or 4,4'-dimethyl biphenyl isomers.

10. A process according to claim 3, further comprising contacting at least part of the raffinate stream with an isomerization catalyst under conditions effective to produce a mixture of isomers comprising the previously extracted dimethyl biphenyl isomer(s).

11. A process according to claim 4, further comprising contacting at least part of one or more of the extract streams with an isomerization catalyst under conditions effective to produce a mixture of isomers comprising the previously extracted dimethyl biphenyl isomer(s).

12. A process according to claim 1, wherein the selective adsorption is performed in the presence of one or more solvents.

13. A process according to claim 12, wherein the solvent comprises an aromatic hydrocarbon, a saturated hydrocarbon or combinations thereof.

14. A process according to claim 1, wherein the first stream comprising the 2,X'-DMBP isomers, where X=2, 3 or 4, further comprises one or more of cyclopentadienyl toluenes (CPDTs), 4-methylcyclohexyl toluenes (4,X'-MCHTs), 3-methylcyclohexyl toluenes (3,X'-MCHTs), 2-methylcyclohexyl toluenes (2,X'-MCHT), ethyl- or dimethyl-cyclopentyl toluenes (CPTs), 1-methylcyclohexyl toluenes (1,X'-MCHTs) and dimethyl bicyclohexanes (DMBCHs).

15. A process according to claim 1, wherein the dehydrogenation product which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) comprises 5-50% by weight 3,3'-isomer, 5-80% by weight 3,4'-isomer and 5-90% by weight 4,4'-isomer based on the total weight of the three isomers.

16. A process according to claim 1, wherein the dehydrogenation product which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) comprises 10-40% by weight 3,3'-isomer, 20-70% by weight 3,4'-isomer and 5-30% by weight 4,4'-isomer based on the total weight of the three isomers.

17. A process according to claim 1, wherein the dehydrogenation product which is separated into at least a first stream comprising one or more 3,3'-, 3,4'- and 4,4'-dimethyl biphenyl isomers and at least one second stream comprising one or more 2,X'-dimethyl biphenyl isomers (where X=2, 3 or 4) comprises 15-35% by weight 3,3'-isomer, 40-70% by weight 3,4'-isomer and 5-30% by weight 4,4'-isomer based on the total weight of the three isomers.

\* \* \* \* \*